US009869636B2

(12) United States Patent
Mander et al.

(10) Patent No.: US 9,869,636 B2
(45) Date of Patent: *Jan. 16, 2018

(54) DEVICE FOR EVALUATION OF FLUIDS USING ELECTROMAGNETIC ENERGY

(71) Applicant: Visualant, Inc., Seattle, WA (US)

(72) Inventors: Richard Ian Mander, Bainbridge Island, WA (US); Allan David Beach, Prebbleton (NZ); Michael Vivian Denton, Christchurch (NZ); Thomas A. Furness, III, Seattle, WA (US); Alan Charles Tompkins, Ferny Grove (AU)

(73) Assignee: Visualant, Inc., Seattle, WA (US)

( * ) Notice: Subject to any disclaimer, the term of this patent is extended or adjusted under 35 U.S.C. 154(b) by 29 days.

This patent is subject to a terminal disclaimer.

(21) Appl. No.: 14/720,241

(22) Filed: May 22, 2015

(65) Prior Publication Data
US 2015/0253244 A1 Sep. 10, 2015

Related U.S. Application Data

(63) Continuation of application No. 13/797,737, filed on Mar. 12, 2013, now Pat. No. 9,041,920.
(Continued)

(51) Int. Cl.
*G01N 21/49* (2006.01)
*G01N 21/05* (2006.01)
(Continued)

(52) U.S. Cl.
CPC ............ *G01N 21/49* (2013.01); *G01N 21/01* (2013.01); *G01N 21/0303* (2013.01);
(Continued)

(58) Field of Classification Search
CPC A61B 5/1455; A61B 5/14532; G01B 3/0297; G01B 21/03; G01B 21/0303;
(Continued)

(56) References Cited

U.S. PATENT DOCUMENTS

| 3,499,158 A | 3/1970 | Lavine et al. |
| 3,504,164 A | 3/1970 | Farrell et al. |

(Continued)

FOREIGN PATENT DOCUMENTS

| EP | 2 266 630 A | 12/2010 |
| GB | 1 470 737 | 4/1977 |

(Continued)

OTHER PUBLICATIONS

"Color Technology Beyond the Visible Spectrum Creating Solutions for Product Authentication: Extraordinary Investment Opportunity & 12 month Roadmap," Visualant Inc., Seattle, Washington, Nov. 17, 2006, 10 pages..

(Continued)

*Primary Examiner* — Dominic J Bologna
(74) *Attorney, Agent, or Firm* — Seed IP Law Group LLP

(57) ABSTRACT

A portable, tabletop fluid sampling device simplifies spectral analysis to produce an accurate but inexpensive chromatic fingerprint for fluid samples. In one embodiment, the sampling device uses an array of variable wavelength LED emitters and photodiode detectors to measure Rayleigh scattering of electromagnetic energy from the fluid sample contained in a cuvette. Either the fluid itself, or particles suspended in the fluid can then be identified by performing spectral pattern matching to compare results of a spectral scan against a library of known spectra. A wide range of applications include substance identification, security screening, authentication, quality control, and medical diagnostics.

18 Claims, 13 Drawing Sheets

Related U.S. Application Data

(60) Provisional application No. 61/767,716, filed on Feb. 21, 2013.

(51) Int. Cl.
 *G01N 21/03* (2006.01)
 *G01N 21/01* (2006.01)
 *G01N 21/59* (2006.01)

(52) U.S. Cl.
 CPC ............ *G01N 21/05* (2013.01); *G01N 21/59* (2013.01); *G01N 2201/022* (2013.01); *G01N 2201/06113* (2013.01)

(58) Field of Classification Search
 CPC ...... G01B 21/274; G01B 21/47; G01B 21/51; G01B 21/65
 See application file for complete search history.

(56) References Cited

U.S. PATENT DOCUMENTS

| | | | |
|---|---|---|---|
| 3,582,659 A | 6/1971 | Dekker | |
| 3,679,449 A | 7/1972 | Nagot et al. | |
| 3,822,098 A | 7/1974 | Rudder et al. | |
| 3,867,039 A | 2/1975 | Nelson | |
| 3,922,090 A | 11/1975 | Fain | |
| 3,942,185 A | 3/1976 | Lebailly | |
| 3,994,590 A | 11/1976 | Di Martini et al. | |
| 4,082,188 A | 4/1978 | Grimmell et al. | |
| 4,098,940 A | 7/1978 | Groh et al. | |
| 4,120,445 A | 10/1978 | Carrier et al. | |
| 4,183,989 A | 1/1980 | Tooth | |
| 4,241,738 A | 12/1980 | Lübbers et al. | |
| 4,277,514 A | 7/1981 | Sugiura et al. | |
| 4,325,981 A | 4/1982 | Sugiura et al. | |
| 4,531,117 A | 7/1985 | Nourse et al. | |
| 4,652,913 A | 3/1987 | Saitoh et al. | |
| 4,678,338 A | 7/1987 | Kitta et al. | |
| 4,760,250 A | 7/1988 | Loeppert | |
| 4,830,501 A | 5/1989 | Terashita | |
| 4,921,278 A | 5/1990 | Shiang et al. | |
| 4,952,061 A | 8/1990 | Edgar | |
| 5,137,364 A | 8/1992 | McCarthy | |
| 5,304,813 A | 4/1994 | De Man | |
| 5,325,167 A | 6/1994 | Melen | |
| 5,353,052 A | 10/1994 | Suzuki et al. | |
| 5,377,000 A | 12/1994 | Berends | |
| 5,576,627 A | 11/1996 | McEwan | |
| 5,619,326 A | 4/1997 | Takamatsu et al. | |
| 5,637,275 A * | 6/1997 | Carey | B01L 3/508 366/214 |
| 5,844,680 A * | 12/1998 | Sperling | G01J 3/50 356/302 |
| 5,924,981 A | 7/1999 | Rothfritz et al. | |
| 5,926,282 A | 7/1999 | Knobloch et al. | |
| 5,933,244 A | 8/1999 | Kiritchenko | |
| 5,946,006 A | 8/1999 | Tajika et al. | |
| 5,966,217 A | 10/1999 | Roe et al. | |
| 5,969,814 A * | 10/1999 | Barber | G01N 21/253 356/338 |
| 6,020,583 A | 2/2000 | Walowit et al. | |
| 6,035,246 A | 3/2000 | Wagner | |
| 6,038,024 A | 3/2000 | Berner | |
| 6,054,021 A | 4/2000 | Kurrle et al. | |
| 6,121,627 A | 9/2000 | Tulip | |
| 6,142,629 A | 11/2000 | Adel et al. | |
| 6,165,609 A | 12/2000 | Curatolo | |
| 6,172,745 B1 | 1/2001 | Voser et al. | |
| 6,176,522 B1 | 1/2001 | Jackson | |
| 6,255,948 B1 | 7/2001 | Wolpert et al. | |
| 6,384,918 B1 | 5/2002 | Hubble, III et al. | |
| 6,421,553 B1 | 7/2002 | Costa et al. | |
| 6,437,326 B1 | 8/2002 | Yamate et al. | |
| 6,439,688 B1 | 8/2002 | Vives et al. | |
| 6,449,045 B1 | 9/2002 | Mestha | |
| 6,494,557 B1 | 12/2002 | Kato et al. | |
| 6,556,932 B1 | 4/2003 | Mestha et al. | |
| 6,560,352 B2 | 5/2003 | Rowe et al. | |
| 6,560,546 B1 | 5/2003 | Shenk et al. | |
| 6,584,435 B2 | 6/2003 | Mestha et al. | |
| 6,621,576 B2 | 9/2003 | Tandon et al. | |
| 6,633,382 B2 | 10/2003 | Hubble, III et al. | |
| 6,639,699 B2 | 10/2003 | Matsuyama | |
| 6,690,465 B2 | 2/2004 | Shimizu et al. | |
| 6,718,046 B2 | 4/2004 | Reed et al. | |
| 6,721,440 B2 | 4/2004 | Reed et al. | |
| 6,721,629 B2 | 4/2004 | Wendling et al. | |
| 6,724,912 B1 | 4/2004 | Carr et al. | |
| 6,731,785 B1 | 5/2004 | Mennie et al. | |
| 6,744,909 B1 | 6/2004 | Kostrzewski et al. | |
| 6,748,533 B1 | 6/2004 | Wu et al. | |
| 6,757,406 B2 | 6/2004 | Rhoads | |
| 6,763,124 B2 | 7/2004 | Alattar et al. | |
| 6,765,663 B2 | 7/2004 | Byren et al. | |
| 6,782,115 B2 | 8/2004 | Decker et al. | |
| 6,788,800 B1 | 9/2004 | Carr et al. | |
| 6,798,517 B2 | 9/2004 | Wagner et al. | |
| 6,804,376 B2 | 10/2004 | Rhoads et al. | |
| 6,804,377 B2 | 10/2004 | Reed et al. | |
| 6,809,855 B2 | 10/2004 | Hubble, III et al. | |
| 6,819,775 B2 | 11/2004 | Amidror et al. | |
| 6,832,003 B2 | 12/2004 | McGrew | |
| 6,835,574 B2 | 12/2004 | Neilson et al. | |
| 6,870,620 B2 | 3/2005 | Faupel et al. | |
| 6,882,737 B2 | 4/2005 | Lofgren et al. | |
| 6,888,633 B2 | 5/2005 | Vander Jagt et al. | |
| 6,930,773 B2 | 8/2005 | Cronin et al. | |
| 6,937,323 B2 | 8/2005 | Worthington et al. | |
| 6,968,337 B2 | 11/2005 | Wold | |
| 6,980,704 B2 | 12/2005 | Kia et al. | |
| 6,992,775 B2 | 1/2006 | Soliz et al. | |
| 6,993,535 B2 | 1/2006 | Bolle et al. | |
| 6,995,839 B1 | 2/2006 | Shapiro | |
| 6,996,478 B2 | 2/2006 | Sunshine et al. | |
| 7,001,038 B2 | 2/2006 | Bock et al. | |
| 7,003,132 B2 | 2/2006 | Rhoads | |
| 7,003,141 B1 | 2/2006 | Lichtermann et al. | |
| 7,005,661 B2 | 2/2006 | Yamaguchi et al. | |
| 7,006,204 B2 | 2/2006 | Coombs et al. | |
| 7,008,795 B2 | 3/2006 | Yerazunis et al. | |
| 7,012,695 B2 | 3/2006 | Maier et al. | |
| 7,016,717 B2 | 3/2006 | Demos et al. | |
| 7,018,204 B2 | 3/2006 | Jung et al. | |
| 7,023,545 B2 | 4/2006 | Slater | |
| 7,026,600 B2 | 4/2006 | Jamieson et al. | |
| 7,027,134 B1 | 4/2006 | Garcia-Rubio et al. | |
| 7,027,165 B2 | 4/2006 | De Haas et al. | |
| 7,027,619 B2 | 4/2006 | Pavlidis et al. | |
| 7,031,555 B2 | 4/2006 | Troyanker | |
| 7,032,988 B2 | 4/2006 | Darby et al. | |
| 7,035,873 B2 | 4/2006 | Weare | |
| 7,038,766 B2 | 5/2006 | Kerns et al. | |
| 7,041,362 B2 | 5/2006 | Barbera-Guillem | |
| 7,044,386 B2 | 5/2006 | Berson | |
| 7,046,346 B2 | 5/2006 | Premjeyanth et al. | |
| 7,046,842 B2 | 5/2006 | Lin et al. | |
| 7,049,597 B2 | 5/2006 | Bodkin | |
| 7,052,730 B2 | 5/2006 | Patel et al. | |
| 7,052,920 B2 | 5/2006 | Ushio et al. | |
| 7,058,200 B2 | 6/2006 | Donescu et al. | |
| 7,058,530 B1 | 6/2006 | Miller et al. | |
| 7,061,652 B2 | 6/2006 | Kurita et al. | |
| 7,063,260 B2 | 6/2006 | Mossberg et al. | |
| 7,130,444 B2 | 10/2006 | Honsinger et al. | |
| 7,154,603 B2 | 12/2006 | Banks | |
| 7,155,068 B2 | 12/2006 | Zhang et al. | |
| 7,170,606 B2 | 1/2007 | Yerazunis | |
| 7,171,680 B2 | 1/2007 | Lange | |
| 7,252,241 B2 | 8/2007 | Yamada | |
| 7,259,853 B2 | 8/2007 | Hubble, III et al. | |
| 7,285,158 B2 | 10/2007 | Iwanami et al. | |
| 7,307,752 B1 | 12/2007 | Mestha et al. | |
| 7,313,427 B2 | 12/2007 | Benni | |

(56) References Cited

U.S. PATENT DOCUMENTS

| | | | |
|---|---|---|---|
| 7,317,814 B2 | 1/2008 | Kostrzewski et al. | |
| 7,319,775 B2 | 1/2008 | Sharma et al. | |
| 7,359,804 B2 | 4/2008 | Williams et al. | |
| 7,383,261 B2 | 6/2008 | Mestha et al. | |
| 7,406,184 B2 | 7/2008 | Wolff et al. | |
| 7,440,620 B1 | 10/2008 | Aartsen | |
| 7,474,407 B2 | 1/2009 | Gutin | |
| 7,483,548 B2 | 1/2009 | Nakano et al. | |
| 7,570,988 B2 | 8/2009 | Ramanujam et al. | |
| 7,616,317 B2 | 11/2009 | Misener et al. | |
| 7,733,490 B2 | 6/2010 | Goodwin et al. | |
| 7,738,235 B2 | 6/2010 | Gloisten et al. | |
| 7,830,510 B2 | 11/2010 | Liu et al. | |
| 7,996,173 B2 | 8/2011 | Schowengerdt et al. | |
| 8,064,286 B2 | 11/2011 | Rønnekleiv et al. | |
| 8,076,630 B2 | 12/2011 | Schowengerdt et al. | |
| 8,081,304 B2 | 12/2011 | Furness, III et al. | |
| 8,285,510 B2 | 10/2012 | Schowengerdt et al. | |
| 8,368,878 B2 | 2/2013 | Furness, III et al. | |
| 8,542,418 B2 | 9/2013 | Chandu et al. | |
| 8,583,394 B2 | 11/2013 | Schowengerdt et al. | |
| 8,796,627 B2 | 8/2014 | Rockwell et al. | |
| 8,872,133 B2 | 10/2014 | Schreiber et al. | |
| 2002/0146146 A1 | 10/2002 | Miolla et al. | |
| 2003/0031347 A1 | 2/2003 | Wang | |
| 2003/0045798 A1 | 3/2003 | Hular et al. | |
| 2003/0063772 A1 | 4/2003 | Smith et al. | |
| 2003/0151611 A1 | 8/2003 | Turpin et al. | |
| 2003/0156752 A1 | 8/2003 | Turpin et al. | |
| 2003/0158617 A1 | 8/2003 | Turpin et al. | |
| 2003/0158788 A1 | 8/2003 | Turpin et al. | |
| 2003/0174882 A1 | 9/2003 | Turpin et al. | |
| 2003/0235919 A1* | 12/2003 | Chandler | G01N 15/1456 422/82.05 |
| 2004/0071311 A1 | 4/2004 | Choi et al. | |
| 2004/0101158 A1 | 5/2004 | Butler | |
| 2004/0101159 A1 | 5/2004 | Butler | |
| 2004/0142484 A1 | 7/2004 | Berlin et al. | |
| 2005/0094127 A1 | 5/2005 | O'mahony et al. | |
| 2006/0059013 A1 | 3/2006 | Lowe | |
| 2006/0077392 A1* | 4/2006 | Hebert | G01N 21/253 356/446 |
| 2006/0161788 A1 | 7/2006 | Turpin et al. | |
| 2007/0078610 A1 | 4/2007 | Adams et al. | |
| 2007/0222973 A1* | 9/2007 | Hoshiko | G01N 21/253 356/39 |
| 2008/0171925 A1 | 7/2008 | Xu et al. | |
| 2008/0212087 A1 | 9/2008 | Mannhardt et al. | |
| 2008/0252066 A1 | 10/2008 | Rapoport et al. | |
| 2011/0223655 A1 | 9/2011 | Lapota et al. | |
| 2012/0037817 A1 | 2/2012 | Vondras et al. | |
| 2012/0072176 A1 | 3/2012 | Schowengerdt et al. | |
| 2012/0288951 A1 | 11/2012 | Acharya et al. | |
| 2013/0208260 A1 | 8/2013 | Furness, III et al. | |
| 2013/0215168 A1 | 8/2013 | Furness, III et al. | |
| 2014/0063239 A1 | 3/2014 | Furness, III et al. | |
| 2014/0203184 A1 | 7/2014 | Purdy et al. | |
| 2014/0218718 A1 | 8/2014 | Mander et al. | |
| 2014/0233015 A1 | 8/2014 | Mander et al. | |
| 2014/0333920 A1 | 11/2014 | Mander et al. | |

FOREIGN PATENT DOCUMENTS

| | | |
|---|---|---|
| JP | 2005-214835 A | 8/1905 |
| JP | 10-508940 A | 9/1998 |
| WO | 91/05459 A1 | 5/1991 |
| WO | 96/07886 A1 | 3/1996 |
| WO | 00/12229 A1 | 3/2000 |
| WO | 03/069884 A2 | 8/2003 |
| WO | 2004/089640 A2 | 10/2004 |
| WO | 2006/050367 A2 | 5/2006 |
| WO | 2008/016590 A2 | 2/2008 |
| WO | 2013/043737 A1 | 3/2013 |
| WO | 2013/119822 A1 | 8/2013 |
| WO | 2013/119824 A1 | 8/2013 |
| WO | 2014/121267 A2 | 8/2014 |
| WO | 2014/130857 A1 | 8/2014 |

OTHER PUBLICATIONS

Cri Nuance Multispectral Imaging System, URL=http://www.cri-inc.com/products/nuance.asp, download date Jan. 30, 2007, 2 pages.

Cri Products Components, URL=http://www.cri-inc.com/products/components.asp, download date Jan. 30, 2007, 5 pages.

Furness III, "Systems, Methods and Articles Related to Machine-Readable Indicia and Symbols," U.S. Appl. No. 61/597,593, filed Feb. 10, 2012, 89 pages.

Furness III, "Area Surveillance Systems and Methods," U.S. Appl. No. 61/597,586, filed Feb. 10, 2012, 72 pages.

Furness, III et al., "Method, Apparatus, and Article to Facilitate Evaluation of Objects Using Electromagnetic Energy," U.S. Appl. No. 60/871,639, filed Dec. 22, 2006, 140 pages.

Furness, III et al., "Method, Apparatus, and Article to Facilitate Evaluation of Objects Using Electromagnetic Energy," U.S. Appl. No. 60/883,312, filed Jan. 3, 2007, 147 pages.

Furness, III et al., "Method, Apparatus, and Article to Facilitate Evaluation of Objects Using Electromagnetic Energy," U.S. Appl. No. 60/890,446, filed Feb. 16, 2007, 155 pages.

Furness, III et al., "Methods, Apparatus, and Article to Facilitate Evaluation of Objects Using Electromagnetic Energy," U.S. Appl. No. 60/834,589, filed Jul. 31, 2006, 135 pages.

International Search Report, dated Jun. 21, 2007, for PCT/US2005/039495, 1 page.

International Search Report, dated Jul. 23, 2008, for PCT/US2007/017082, 1 page.

International Search Report, dated Feb. 25, 2013, for PCT/US2012/056135, 3 pages.

International Search Report, dated May 15, 2013, for PCT/US2013/025162, 3 pages.

International Search Report, dated May 13, 2013, for PCT/US2013/025164, 3 pages.

International Search Report and Written Opinion, dated Jun. 19, 2014, for PCT/US2014/017776, 11 pages.

International Search Report, mailed Dec. 8, 2014, for PCT/US14/14656, 2 pages.

International Search Report, dated Sep. 4, 2014, for PCT/US2014/024100, 3 pages.

Japanese Office Action with English Translation for Corresponding Japanese Patent Application No. 2009-522834, dated Aug. 7, 2012, 8 pages.

Mander et al., "A Device for Evaluation of Fluids Using Electromagnetic Energy," U.S. Appl. No. 61/767,716, filed Feb. 21, 2013, 61 pages.

Mander et al., "Method, Apparatus, and Article to Facilitate Evaluation of Substances Using Electromagnetic Energy," U.S. Appl. No. 61/760,527, filed Feb. 4, 2013, 72 pages.

Mander et al., "Systems and Methods for Fluid Analysis Using Electromagnetic Energy," U.S. Appl. No 61/777,750, filed Mar. 12, 2013, 39 pages.

Purdy, "Fluid Medium Sensor System and Method," U.S. Appl. No. 61/538,617, filed Sep. 23, 2011, 75 pages.

Schowengerdt et al., "Method, Apparatus, and Article to Facilitate Distributed Evaluation of Objects Using Electromagnetic Energy," U.S. Appl. No. 60/834,662, filed Jul. 31, 2006, 96 pages.

Schowengerdt et al., "System and Method of Evaluating an Object Using Electromagnetic Energy," U.S. Appl. No. 60/820,938, filed Jul. 31, 2006, 69 pages.

Schowengerdt, "Brief Technical Description of the Cyclops Spectral Analysis and Authentication System," Visualant Inc. memorandum, not disclosed prior to Dec. 22, 2006, 2 pages.

Thomas, "A Beginner's Guide to ICP-MS—Part V: The Ion Focusing System," *Spectroscopy* 16(9):38-44, Sep. 2001.

Turpin et al., "Full Color Spectrum Object Authentication Methods and Systems," U.S. Appl. No. 60/732,163, filed Oct. 31, 2005, 198 pages.

(56) References Cited

OTHER PUBLICATIONS

Turpin, "Full Color Spectrum Object Authentication Methods and Systems," U.S. Appl. No. 60/623,881, filed Nov. 1, 2004, 114 pages.
Vrhel, "An LED based spectrophotometric instrument," *Color Imaging: Device-Independent Color, Color Hardcopy, and Graphic Arts IV, Proceedings of the SPIE 3648*:226-236, Jan. 1999.
Written Opinion, dated Jun. 21, 2007, for PCT/US2005/039495, 5 pages.
Written Opinion, dated Jul. 23, 2008, for PCT/US2007/017082, 3 pages.
Written Opinion, dated Feb. 25, 2013, for PCT/US2012/056135, 4 pages.
Written Opinion, dated May 15, 2013, for PCT/US2013/025162, 7 pages.
Written Opinion, dated May 13, 2013, for PCT/US2013/025164, 6 pages.
Written Opinion, dated Dec. 8, 2014, for PCT/US14/14656, 10 pages.
Written Opinion, dated Sep. 4, 2014, for PCT/US2014/024100, 4 pages.

\* cited by examiner

DEVICE FOR EVALUATION OF FLUIDS USING ELECTROMAGNETIC ENERGY

BACKGROUND

Field

This disclosure generally relates to evaluation systems, and more particularly to systems that evaluate characteristics of substances using electromagnetic energy.

Description of the Related Art

Various systems employ spectral analysis returned from a sample of a substance to analyze the sample and/or recognize the substance.

For example, U.S. Pat. No. 8,076,630 describes systems and methods of evaluating objects using electromagnetic energy. In particular, U.S. Pat. No. 8,076,630 teaches a system for evaluating subject objects, the system which includes at least one physical source operable to emit electromagnetic energy and driver electronics drivingly coupled to at least one physical source. The driver electronics drive at least one physical source as a number of logical sources, using an electromagnetic forcing function where the number of logical sources is greater than the number of physical sources. In addition, the system includes a sensor to receive an electromagnetic response from at least a portion of an evaluation object illuminated by one or more physical sources operated as logical sources, and convert the electromagnetic response to a test response signal indicative of the electromagnetic response of the evaluation object.

Also for example, U.S. Pat. No. 7,996,173 describes methods, apparatus and articles to facilitate distributed evaluation of objects using electromagnetic energy. In particular, U.S. Pat. No. 7,996,173 teaches that objects such as manufactured goods or articles, works of art, media such as identification documents, legal documents, financial instruments, transaction cards, other documents, and/or biological tissue are sampled via sequential illumination in various bands of the electromagnetic spectrum, and a test response to the illumination is analyzed with respect to reference responses of reference objects. U.S. Pat. No. 7,996,173 teaches that the sequence may be varied. For instance, the sequence may define an activation order, a drive level and/or temperature for operating one or more sources. Illumination may be in visible, infrared, ultraviolet, or other portions of the electromagnetic spectrum. U.S. Pat. No. 7,996,173 further teaches that elements of the evaluation system may be remote from one another, for example communicatively coupled via a network.

As a further example, U.S. Pat. No. 8,081,304 describes the use of spectral information in process control and/or quality control of goods and articles. In particular, U.S. Pat. No. 8,081,304 describes the use of spectral information in process control and/or quality control of media, for example financial instruments, identity documents, legal documents, medical documents, financial transaction cards, and/or other media, fluids for example lubricants, fuels, coolants, or other materials that flow, and in machinery, for example vehicles, motors, generators, compressors, presses, drills and/or supply systems. U.S. Pat. No. 8,081,304 further describes the use of spectral information in identifying biological tissue and/or facilitating diagnosis based on biological tissue.

The above described patents are only representative.

BRIEF SUMMARY

It may be useful to analyze fluids, in particular, to determine various physical characteristics of the fluids and/or to recognize the fluid as carrying or not carrying a specific type of substance. In order to reliably analyze and/or recognize a fluid or a substance within the fluid, it may be useful to sample the fluid at a relatively large number of distinct wavelengths or bands of wavelengths of electromagnetic energy. The wavelengths may for example include some or all wavelengths in an optical portion of the electromagnetic spectrum, from near-infrared (N-IR) to near-ultraviolet (N-UV), inclusive, including a visible portion that is visually perceptible to humans. Accurately performing such analysis or recognition typically requires a relatively large number of distinct sources or emitters, e.g., solid-state sources of electromagnetic energy such as light emitting diodes (LEDs), each operable to emit electromagnetic energy in a respective range or band of wavelengths which may or may not partially overlap with one another.

To achieve a high degree of reliability it may be advantageous to perform calibration. Calibration can address issues raised by variations in source performance, for example variations in emitter wavelength output due to age, changes in temperature, or even in manufacturing tolerances (e.g., from batch to batch from a given emitter manufacturer). However, to be effective calibration will typically need to be performed automatically, preferably with little to no user or operator interaction. Also, to be effective calibration with respect to sources or emitters should employ calibration targets or samples with known characteristics (e.g., spectral characteristics) which are stable and do not vary over time.

Providing for automatic calibration may enhance the accuracy of sampling devices. Providing for automatic calibration in a compact form factor may further allow for small, portable sampling devices, which are highly accurate.

Scattering is a physical process in which some forms of electromagnetic energy deviate from a straight path or trajectory due to localized non-uniformities in a medium through which the electromagnetic energy passes. As commonly used, this also includes deviation of reflected electromagnetic energy from an angle predicted by the law of reflection. Reflections that undergo scattering are often called diffuse reflections, while unscattered reflections are called specular (e.g., mirror-like) reflections.

Electromagnetic scattering mechanisms include, for example, Rayleigh scattering and Raman scattering. In Rayleigh scattering most photons are elastically scattered such that the scattered photons have the same kinetic energy, and therefore the same wavelength, as the incident photons. In Raman scattering, photons are scattered by excitation, so that the scattered photons have a frequency that is different from, and usually lower than, that of the incident photons. For any given sample both mechanisms will typically apply, with Raman scattering making up a smaller fraction of the total scattering. Raman scattering is particularly useful in analyzing composition of liquids, gases and solids.

Lambertian reflectance characterizes an ideal diffusely reflecting surface. An apparent brightness of such an ideal diffusely reflecting surface is the same regardless of angle of view. Technically, the luminance of a surface is isotropic, and luminous intensity obeys Lambert's cosine law. Lambertian reflection from polished (i.e., glossy or non-matte) surfaces is typically accompanied by specular reflection. The luminance of a polished or glossy surface is largest when viewed at a perfect reflection direction, for example, normal to the surface (i.e., where a direction of the reflected light is a reflection of the direction of the incident light in the surface). The luminance falls off sharply as direction (i.e., angle) changes.

An undisturbed surface of a liquid exhibits specular (mirror-like) reflection. To achieve a high degree of accuracy, in some implementations it may be advantageous to eliminate specular reflection or at least allow discrimination between scattered and specular reflection. Such reflection may be from a sample or specimen itself, a surface on which the sample or specimen resides, or even a component of a sampling device, for instance a protective window or lens cover. To achieve a high degree of accuracy, in some implementations it may be advantageous to separate specular reflection from diffuse reflection, detecting each separately.

Sampling devices employing automatic calibration and/or separation of specular reflection may be effective employed in the object analysis, evaluation or identification to various applications, for example: manufacturing process control, quality assurance, media authentication, biological tissue recognition, identification, verification, authentication, classification, and/or diagnostics.

A sampling device may be summarized as including a housing; a sample chamber in the housing, the sample chamber sized and dimensioned to receive a sample cuvette at least partially therein, the sample chamber having at least one opaque wall and at least a first aperture and a second aperture positioned at least partially across at least a portion of the sample chamber from the first aperture, the first and the second aperture transmissive of electromagnetic energy of at least some wavelengths in an optical portion of the electromagnetic spectrum; a plurality of emitters received in the housing, each of the emitters selectively operable to emit electromagnetic energy in a respective range of wavelengths toward and through the first aperture of the sample chamber, the ranges of wavelengths of at least some of the emitters different from the ranges of wavelengths of others of the emitters; at least one primary sampling sensor positioned to receive electromagnetic energy emitting from the sample chamber via the second aperture; and at least one calibration sensor positioned to receive electromagnetic energy emitted by at least one of the emitters, substantially free of electromagnetic energy emitting, if any, from the sample chamber.

The sampling device wherein there may be formed a slit in a calibration printed circuit board (PCBA) opposed to the emitters, and the at least one calibration sensor may include at least a first calibration sensor positioned to one side of the slit and at least a second calibration sensor positioned to another side of the slit, the other side of the slit disposed across the slit from the first side of the slit. The emitters may all be aligned with the first aperture. The at least one calibration sensor may be positioned at least adjacent a first portion of the sample chamber opposed to the emitters. The emitters may be carried by an emitter circuit board, the emitter circuit board spaced from the sample chamber opposed to the first aperture. At least one of the primary sampling sensors may be carried by a direct sensor circuit board, the direct sensor circuit board spaced from the sample chamber opposed to the second aperture. The sample chamber may include a third aperture, the third aperture positioned at least partially across the sampling chamber from both the first and the second apertures, and the at least one primary sampling sensor may include at least a first primary sampling sensor positioned to receive electromagnetic energy emitting from the sampling chamber via the second aperture and at least a second primary sampling sensor positioned to receive electromagnetic energy emitting from the sampling chamber via the third aperture. The second aperture may be diametrically opposed across the sample chamber from the first aperture and the third aperture may be non-collinear with an optical axis that extends between the first and the second apertures. The third aperture may be positioned along an axis perpendicular to the optical axis that extends between the first and the second apertures. The emitters may be carried by an emitter circuit board, the emitter circuit board spaced from the sample chamber opposed to the first aperture, at least the first primary sampling sensors may be carried by a direct sensor circuit board, the direct sensor circuit board spaced from the sample chamber opposed to the second aperture, and at least the second primary sampling sensors may be carried by an indirect sensor circuit board, the indirect sensor circuit board spaced from the sample chamber opposed to the third aperture to capture electromagnetic energy scattered from the sample chamber. The sampling device may further include a biasing member such as, for example, a spring that biases at least the sample cuvette outwardly from the housing. The respective ranges of wavelengths of at least two of the emitters may at least partially overlap. The sampling device may further include the sample cuvette sized and dimensioned to be at least partially received by the sample chamber, at least a portion of the sample cuvette transmissive to at least some of the wavelengths of electromagnetic energy emitted by the emitters. The optical portion of the electromagnetic spectrum may extend from near-infrared through near-ultraviolet. The sampling device may further include at least one port providing flow through fluid communication with the cuvette. The sampling device may further include at least one control subsystem communicatively coupled to the emitters, the primary sampling sensors; and the calibration sensors; and at least one temperature sensor communicatively coupled to the at least one control subsystem, wherein the at least one control subsystem controls operation based at least in part on information from both the calibration sensors and the at least one temperature sensor. The at least one control subsystem may calibrate an output value based at least in part on information from both the calibration sensors and the at least one temperature sensor. The at least one control subsystem may calibrate a drive signal supplied to at least one of the emitters based at least in part on information from both the calibration sensors and the at least one temperature sensor.

A sampling device may be summarized as including a housing; a sample chamber in the housing, the sample chamber sized and dimensioned to receive a sample cuvette at least partially therein, the sample chamber having at least one opaque wall and at least a first aperture, a second aperture positioned at least partially across at least a portion of the sample chamber from the first aperture, and a third aperture, the third aperture positioned at least partially across the sampling chamber from both the first and the second apertures, the first, the second, and the third apertures transmissive of electromagnetic energy of at least some wavelengths in an optical portion of the electromagnetic spectrum; a plurality of emitters received in the housing, each of the emitters selectively operable to emit electromagnetic energy in a respective range of wavelengths toward and through the first aperture of the sample chamber, the ranges of wavelengths of at least some of the emitters different from the ranges of wavelengths of others of the emitters; at least one direct primary sampling sensor positioned to receive electromagnetic energy emitting from the sampling chamber via the second aperture and not by the first or the third apertures; and at least one indirect primary sampling sensor positioned to receive electromagnetic energy emitting from the sampling chamber via the third aperture and not by the first or the second apertures.

The second aperture may be diametrically opposed across the sample chamber from the first aperture. The third aperture may be non-collinear with an optical axis that extends between the first and the second apertures. The third aperture may be perpendicular to an optical axis that extends between the first and the second apertures. The emitters may be carried by an emitter circuit board, the emitter circuit board spaced from the sample chamber opposed to the first aperture, at least the first primary sampling sensor may be carried by a direct sensor circuit board, the direct sensor circuit board spaced from the sample chamber opposed to the second aperture, and at least the second primary sampling sensor may be carried by an indirect sensor circuit board, the indirect sensor circuit board spaced from the sample chamber opposed to the third aperture to capture electromagnetic energy scattered from the sample chamber. The sampling device may further include at least one calibration sensor positioned to receive electromagnetic energy emitted by at least one of the emitters, substantially free of electromagnetic energy emitting, if any, from the sampling chamber. The sampling device may further include at least one control subsystem communicatively coupled to the emitters, the primary sampling sensors; and the calibration sensors; and at least one temperature sensor communicatively coupled to the at least one control subsystem, wherein the at least one control subsystem controls operation based at least in part on information from both the calibration sensors and the at least one temperature sensor. The at least one control subsystem may calibrate an output value based at least in part on information from both the calibration sensors and the at least one temperature sensor. The sampling device may further include a biasing member that biases at least the sample cuvette outwardly from the housing. The respective range of wavelengths of at least two of the emitters may at least partially overlap. The sampling device may further include the sample cuvette sized and dimensioned to be at least partially received by the sample chamber, at least a portion of the sample cuvette transmissive to at least some of the wavelengths of electromagnetic energy emitted by the emitters. The optical portion of the electromagnetic spectrum may extend from near-infrared through near-ultraviolet. The sampling device may further include at least one port providing flow through fluid communication with the cuvette.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems, networks, servers, microprocessors, memories, buses, sources of electromagnetic energy, and/or detectors or sensors have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to recognize, identify, verify, authenticate and/or classify objects has numerous commercial applications.

It may be useful to determine analyze characteristics of a sample or specimen being evaluated. For example, it may be useful to determine whether a sample or specimen being evaluated is identical or similar to a previously evaluated sample or specimen, for instance a reference sample or specimen. Also for example, it may be useful to determine if a sample or specimen is identical to a previously evaluated sample or specimen.

Figure 1:
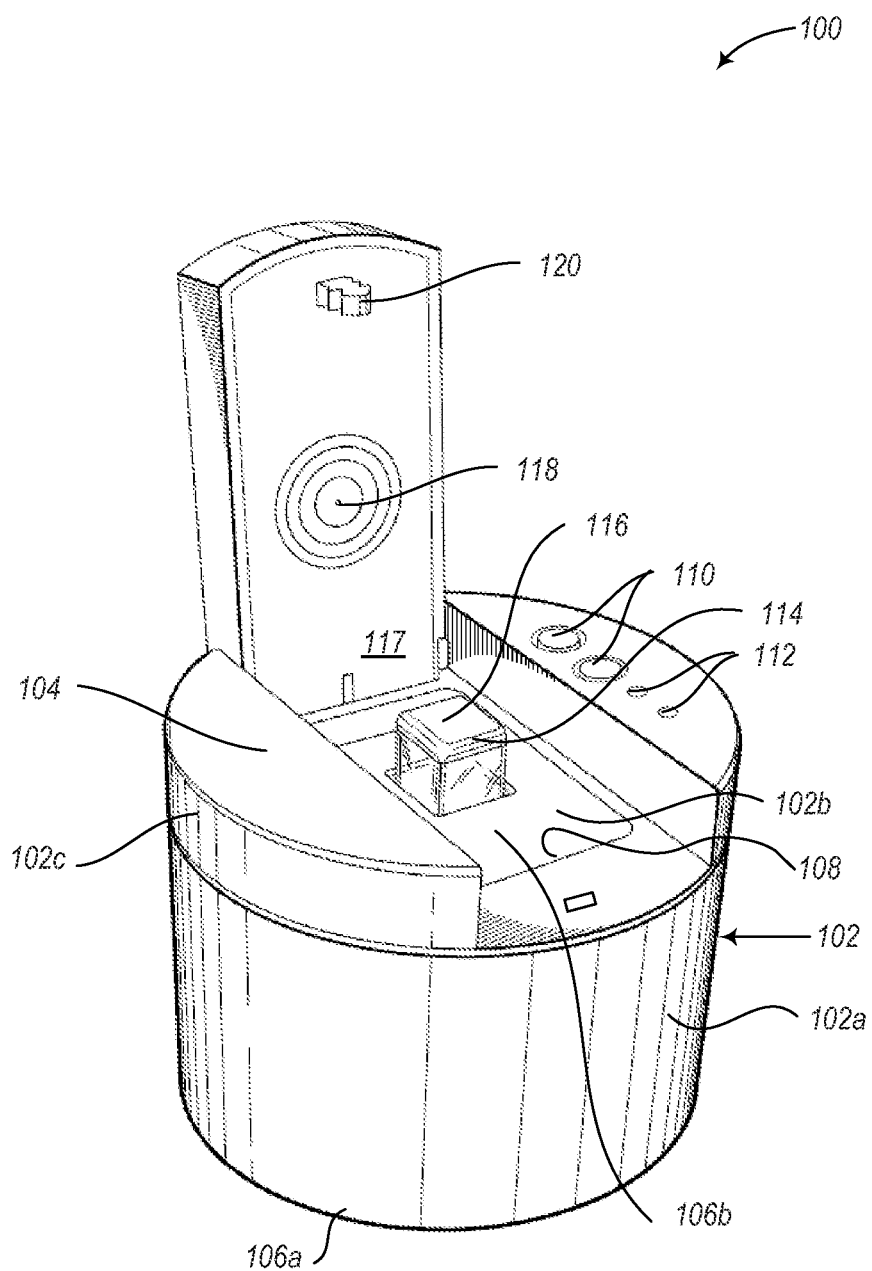
FIG. 1 is an isometric view of the exterior of a fluid sampling device with a hinged lid in the fully open position, according to one illustrated embodiment.
Figure 2:
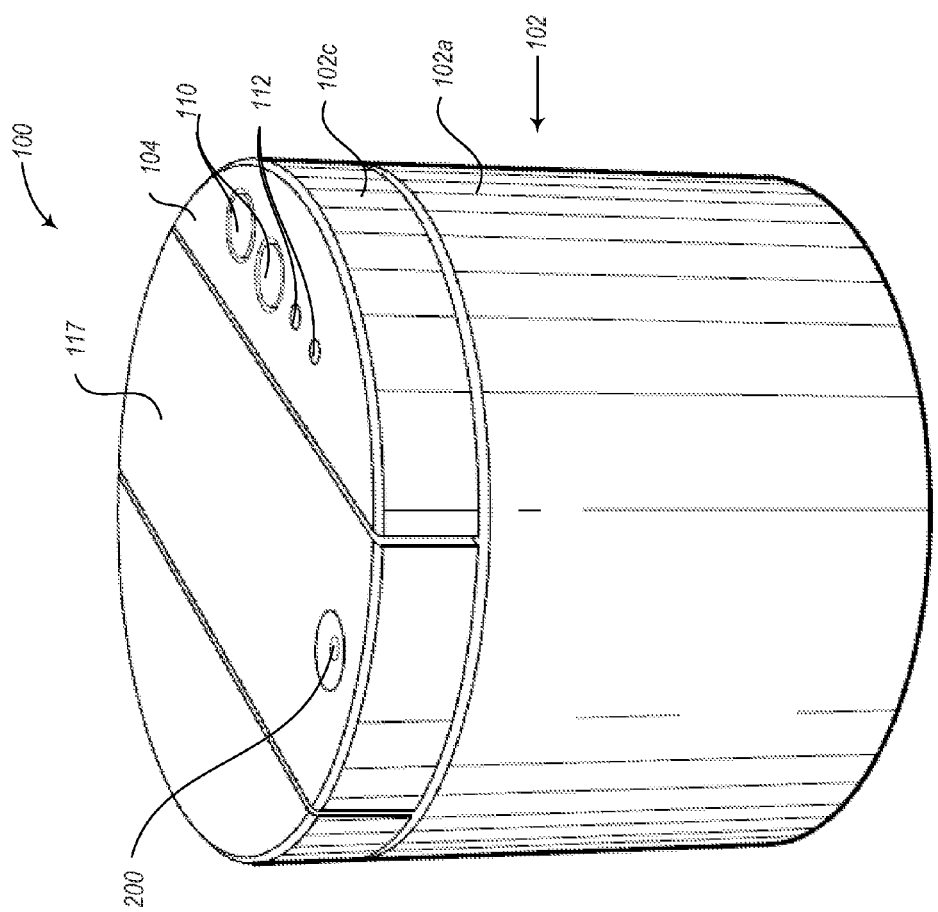
FIG. 2 is a pictorial perspective view of the exterior of a fluid sampling device with a hinged lid in the closed position, according to one illustrated embodiment.

Referring to FIGS. 1 and 2, a fluid sample or specimen analysis or evaluation device 100 is shown according to one illustrated embodiment, referred to herein simply as sampling device 100. Types of fluids that can be accommodated by the sampling device 100 include liquids, and highly viscous materials such as gels, slurries, pastes, and the like. Liquids include pure liquids and liquids containing particulates such as, for example, colloidal suspensions. Some examples of the sampling device 100 can accommodate other types of fluid samples such as aerosols or other suspensions of liquid droplets or solid particles in a gas (e.g., sprays). Other examples of the sampling device 100 can include gases themselves (pressurized or un-pressurized (e.g., air, or atmospheric samples). However, because the sampling device 100 may be used more often to analyze liquids, the sampling device 100 can be referred to as a liquid scanner.

As discussed in detail below, the sampling device 100 is operable to sequentially illuminate a fluid sample with a number of bands of electromagnetic energy. The sampling device 100 is also operable to detect, measure or otherwise capture electromagnetic energy reflected, emitted, fluoresced, refracted, diffracted or otherwise transmitted, or otherwise returned from the fluid sample in response to the illumination. As used herein and in the claims, the terms illuminate, illuminates, illumination, and variations of such terms mean to expose to or reveal by the use of electromagnetic energy or electromagnetic energy, whether in the visible portion of the electromagnetic spectrum, the optical portion (e.g., visible, near-infrared, near-ultraviolet), or other portions (e.g., far-infrared, far-ultraviolet, microwave, X-ray, etc.).

The sampling device 100 includes a housing 102 which, in the illustrated embodiment, includes a tubular (e.g., cylindrical) main body housing portion 102a, a sample chamber 102b in the main body housing portion 102a, and a cap 102c having a top surface 104. The housing 102 may, for example, be sized and dimensioned as a portable tabletop unit that can be hand carried from one location to another. Furthermore, such a table top unit is intended to be accessible and affordable to a wider range of users than are existing laboratory-based models.

The main housing portion 102a has a housing base 106a and a housing top 106b opposite the housing base 106a. The main housing portion 102a has a side wall 108 surrounding the sample chamber 102b which is adjacent to an exterior surface of the main housing portion 102a. The top end 106b can be exposed by opening exemplary hinged lid 117 to provide selective access to the sample chamber 102b. The main housing portion 102a may be comprised of any of a large variety of materials, for example ABS plastic, other plastics, metals (e.g., aluminum) and/or composite materials (e.g., carbon fiber impregnated resin). The main body housing portion 102a may be sized and dimensioned to be easily held and operated by a person using a single hand. While illustrated as a cylinder, the main body housing portion 102a may take any variety of shapes.

The sampling device 100 may also include one or more function buttons 110 which are operable from an exterior of the sampling device 100, for example, from the cap 102c. The function buttons 110 may take any of a large variety of forms, other than push-buttons, (e.g., slidable switches, rotatable selectors, and the like). For example, a contact or slideable switch may be actuatable via a window, slot or other aperture in the housing 102. Additionally or alternatively, a touch sensitive switch may be employed, for instance an inductive or a capacitive switch. The function buttons 110 may be responsive to actuation to send a signal, or otherwise cause the sampling device to execute a sampling operation. As discussed in detail below, the sampling operation may be preceded by a calibration operation.

The sampling device 100 may further include one or more visual indicators (e.g., light emitting diodes or LEDs, two shown collectively referenced as 112), shown in FIGS. 1, 2 as located on an upper surface 104 of the cap 102c. The visual indicators 112 may indicate a status or mode of the sampling device (e.g., "ready" or "power on"), for instance via different colors (e.g., green, red, amber) and or patterns (e.g., flashes). Or, one or more light communicative paths (e.g., optical fiber or light pipes) may communicatively couple light to the visual indicators 112. Additionally or alternatively, visual indicators 112 may be located anywhere on the housing 102, or underneath a window (not shown) mounted anywhere on the surface of the housing 102.

The sample chamber 102b is sized and dimensioned to at least partially receive, as shown in FIG. 1, a specimen container referred to as a sample cuvette 114. The sample cuvette 114 may be made of any of a large variety of materials transmissive (i.e., transparent or at least translucent) to at least those wavelengths of electromagnetic energy (e.g., UV) which are used in the analysis or evaluation of a sample or specimen. Such materials may include, for example, silica (i.e., fused quartz) or a cyclic polyolefin commercially available from Zeon Chemicals of Louisville, Ky. under the trademark Zeonex®, for example having minimal absorption characteristics for wavelengths between approximately 330 nm and extending to or beyond approximately 1,200 nm. Material transparency may vary with the choice of wavelengths used for illumination. In addition, containment of different fluids may require different materials. A plurality of different cuvette types may therefore be accommodated by the sampling device 100. While illustrated as a square cylindrical tube, the sample cuvette 114 and sample chamber 102b may take any variety of shapes. An advantage of the square cylindrical tube is the avoidance of focusing, refracting, or diffracting certain electromagnetic wavelengths. The sampling device 100 can further include a port providing flow through fluid communication with the sample cuvette 114.

The sample cuvette 114 has a removable cuvette lid 116 that need not be transparent. The cuvette lid 116 is desirably made of, or includes a material such as rubber, silicone, or another similar elastic material. The cuvette lid 116 can thus be capable of forming a seal against the sample cuvette 114 to prevent leakage of the fluid sample.

The cap 102c can also include an access panel such as a hinged lid 117 that opens to allow access for an operator to load the sample cuvette 114 into the sample chamber 102b. Alternatively, the access panel could take the form of a sliding cover, a fully removable cover, or any number of other lid designs.

The exemplary hinged lid 117 is shown in FIG. 1 in an open position, and in FIG. 2 in a closed position. The hinged lid 117 can include a stabilizing feature 118 that helps to hold the sample cuvette 114 in a fixed position. The hinged lid 117 can further include a latch 120 that holds the hinged lid 117 securely closed during a sample analysis run. The securing engagement may be selectively releasable under a moderate application of pulling force or tension on the hinged lid 117. Additionally or alternatively, the hinged lid 117 can be released by an operator action such as, for example, pressing one or both of the function buttons 110.

Figure 3:
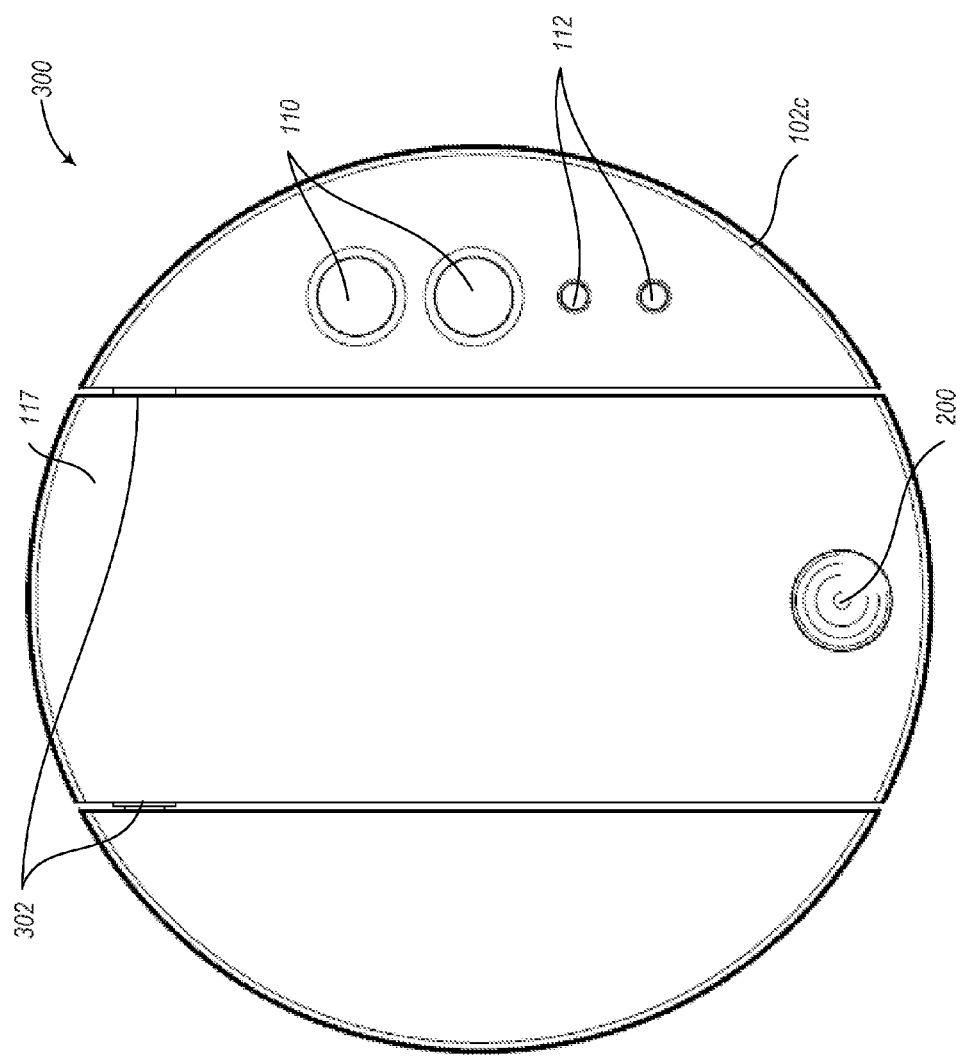
FIG. 3 is a top plan view of the exterior of a fluid sampling device according to one illustrated embodiment.

As shown in FIG. 2, a finger indentation 200 can be provided in the top surface of the hinged lid 117 to facilitate selective opening and/or secure closure by applying pressure directly over the latch 120. The hinged lid 117 can be coupled to the sample cuvette 114 such that when the hinged lid 117 is closed, the sample cuvette 114 is held down in a fixed position within the sample chamber 102b. When the hinged lid 117 is in an open position, the sample cuvette 114 can be automatically released by a biasing member (e.g., spring) so that the sample cuvette 114 pops up out of the sample chamber 102b for ease of removal. While FIGS. 1 and 2 indicate certain shapes and/or dimensions (e.g., a cylindrical housing) which may be suitable for some embodiments, the sampling device 100 may employ other shapes and/or dimensions. Thus, the specified shapes and/or dimensions should not be considered limiting. FIG. 3 presents a view 300 of the housing cap 102c, showing a pair of hinges 302 about which the hinged lid 117 pivots. In one embodiment, the hinges 302 are located near the perimeter of the cap 102c. It is noted that any number of alternative lid configurations can be substituted for the hinged lid 117 shown.

Figure 4:
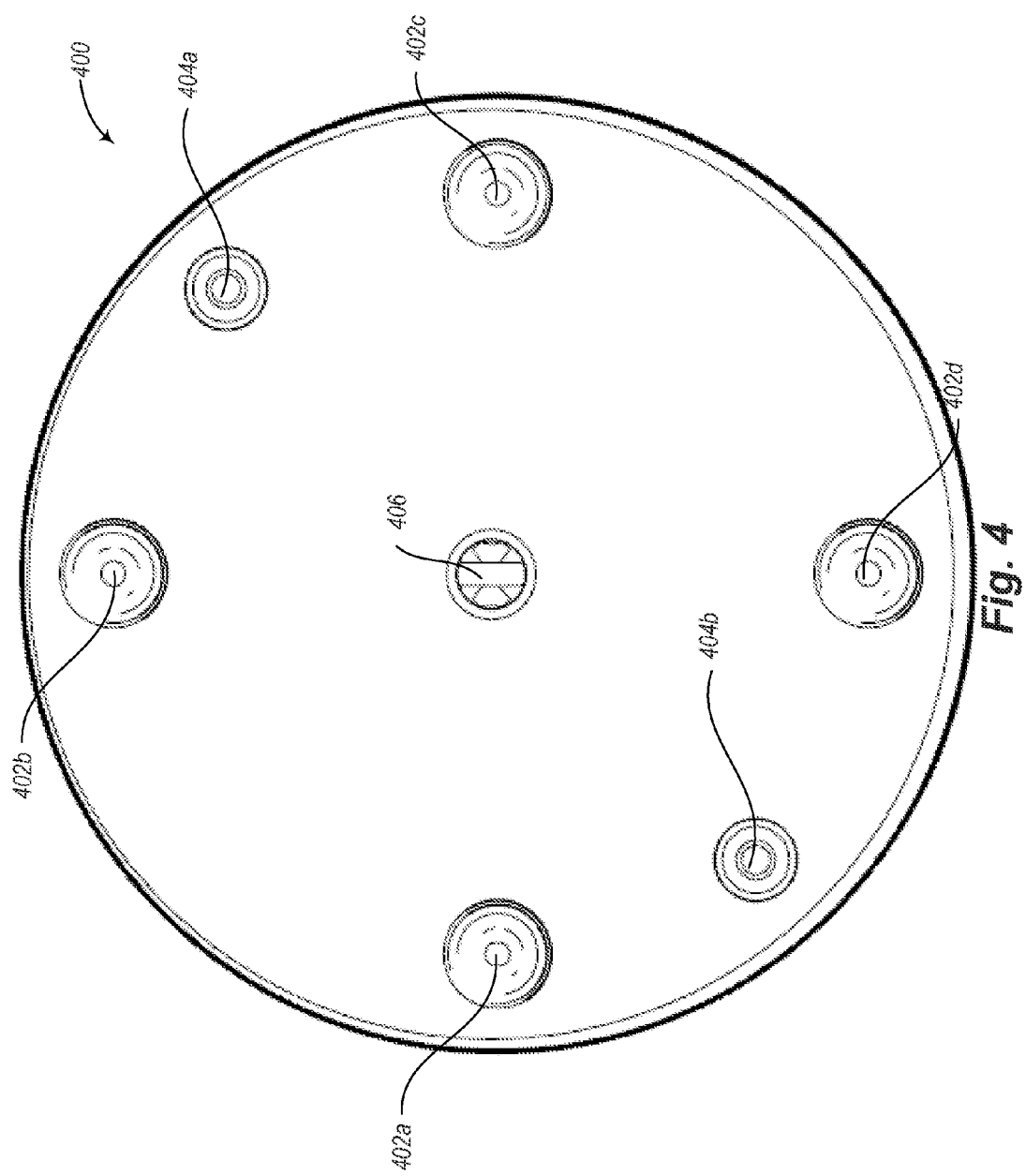
FIG. 4 is a bottom plan view of the exterior of a fluid sampling device according to one illustrated embodiment.

FIG. 4 depicts a view 400 of the housing 102, showing a plurality of feet 402a, 402b, 402c, and 402d, (four shown, collectively 402) on which the sampling device 100 can rest on a table top or desk top, for example. Also shown in FIG. 4 is a pair of screws 404a and 404b (two shown, collectively 404) and a drain hole 406. The drain hole 406 can prevent any liquid that may escape both the sample cuvette 114 and the sample chamber 102b from accumulating inside the housing 102.

Figure 5:
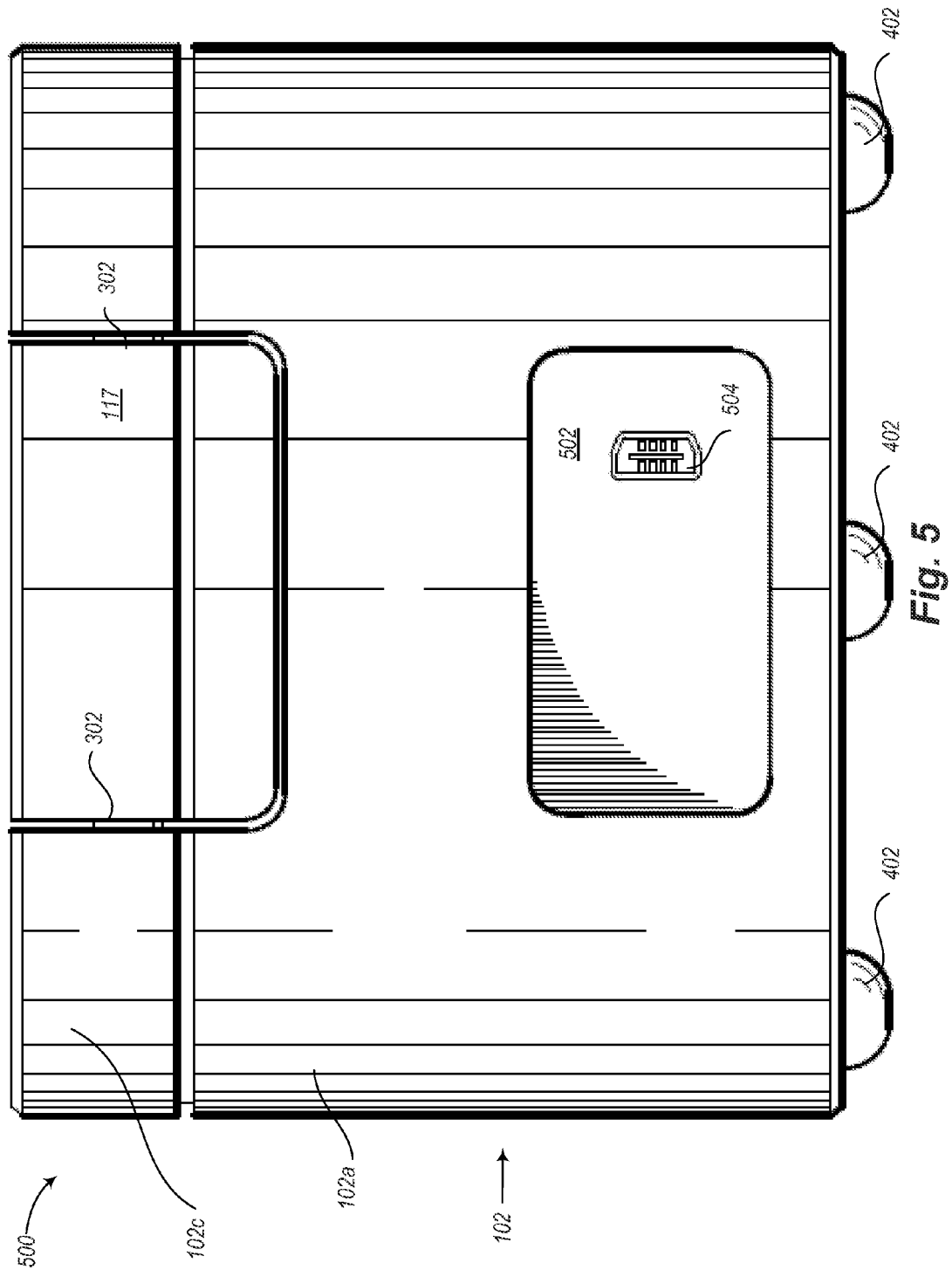
FIG. 5 is a side elevation view of the exterior of a fluid sampling device, in which a communications port is shown, according to one illustrated embodiment.

FIG. 5 shows a view 500 of the back of the sampling device 100, in which is shown a panel 502 surrounding a cable receptacle 504. The panel 502 may be a removable access panel. While the cable receptacle 504 is pictured as a USB port it is not so limited. One or more other types of communications ports and/or power supply connections, or combinations thereof, may be provided in conjunction with the panel 502. Such connections may provide pathways for power delivery and uni-directional or bi-directional data flow to support the functions of the sampling device 100. Alternatively, or in addition, power and/or data connections to the sampling device 100 can be partly or fully wireless, thereby allowing data upload to a Web site via the Internet, for example. Instructions may also be received by the sampling device via the cable receptacle 504 or via a wireless connection.

Figure 6:
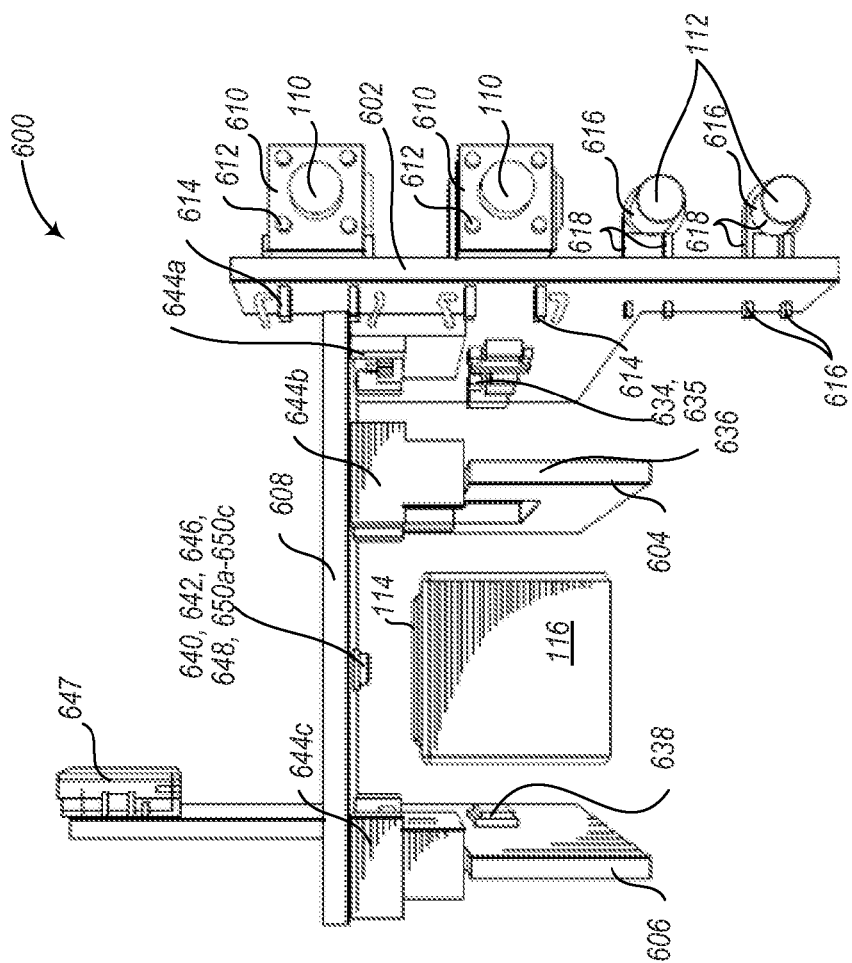
FIG. 6 is a top perspective view of a parts assembly shown removed from the housing of a fluid sampling device, according to one illustrated embodiment.

FIG. 6 shows a view 600 of internal parts within the sampling device 100 relative to the sample cuvette 114. In the center is shown the top surface of the cuvette lid 116. Inside the illustrated sampling device 100 are shown four printed circuit board assemblies (PCBAs): a transducer PCBA 602, a calibrator PCBA 604, a direct sensor PCBA 606, and a backplane PCBA 608, which also serves as an indirect sensor PCBA. In the embodiment shown, the PCBAs 602, 604, and 606 are oriented substantially parallel to one another and substantially perpendicular to the backplane PCBA 608, to which they connect. This orientation of the PCBAs provides a rigid structure that helps to direct the electromagnetic energy path. As illustrated, the backplane PCBA 608 may be sized and dimensioned to be securely received in housing 102, for example engaging an inner periphery of the housing base 106a, an inner periphery of the side wall 108, or other attachment structures. Engagement may be via a press fit or via some coupling structure such as a detent structure, or a clip as shown below in FIG. 12 to secure the PCBAs 602, 604, and 606.

The PCBAs 602, 604, 606, and 608 may comprise any of a large variety of materials, for example plastics metals, or composite materials. The PCBAs are typically opaque or substantially opaque, at least to electromagnetic energy that is employed in the analysis or evaluation of the samples or specimens. The PCBAs may, for example, be painted black, coated black, or may include black pigments.

According to one embodiment, the function buttons 110 and visual indicators 112 are shown mounted to the top of the transducer PCBA 602. The function buttons 110 are further shown attached to function button support plates 610 via function button fasteners 612. The function button support plates 610 are coupled to the transducer PCBA 602 by function button coupling pins 614 that are through-hole mounted to the transducer PCBA 602. Electrical connections from the function buttons 110 are also coupled to internal electronic and/or electrical components via the transducer PCBA 602. Similarly, the visual indicators 112 are attached to indicator support plates 616, and the indicator support plates 616 are coupled to the transducer PCBA 602 via indicator coupling pins 618. Other form factors for the function buttons 110, visual indicators 112, and associated connections, or an alternative user interface can be substituted for those shown.

As explained in more detail below, the transducer PCBA 602 includes a plurality of transducers, typically in the form of a plurality of emitters (seven shown, collectively 634). The calibrator PCBA 604 includes one or more calibration detectors or sensors (four shown, collectively 636). The direct sensor PCBA 606 includes one or more first primary sampling detectors or sensors (four shown, collectively 638). Also as explained in more detail below, the backplane PCBA 608 includes one or more second primary sampling detector(s) or sensor(s) (four shown, collectively 640), and various other electrical and electronic components (collectively 642) to control operation of the sampling device 100 and/or communications therefrom. The transducer PCBA 602, the calibrator PCBA 604, and the direct sensor PCBA 606 each include a respective coupler or connector 644a, 644b, and 644c, respectively, to communicatively couple electronic and/or electrical components or circuits of the each of the PCBAs 602, 604, and 606 with the components or circuits of the backplane PCBA 608. Accordingly, the backplane PCBA 608 can be configured with a plurality of sockets for receiving the connectors 644a, 644b, and 644c. Connectors 644a, 644b, and 644c may be slot connectors having a slot sized and dimensioned to mate with a coupler of the transducer PCBA 602, for instance an edge or tab. Each of the couplers or connectors 644a, 644b, and 644c typically carry a variety of electrical contacts, although other signal transfer structures (e.g., optical fiber) can be employed.

Power can also be supplied to each of the PCBAs 602, 604, and 606 through the connectors 644a, 644b, and 644c. A power source (not shown) may take the form of a portable power source, for example one or more batteries, fuel cells, and/or super- or ultra-capacitors. Additionally, or alternatively, the power source may take the form of a fixed power source, such as a cable plugged into a port of a computer (e.g., USB cable) or a conventional electrical receptacle (e.g., wall outlet).

The backplane PCBA 608 may, for example, optionally include a control subsystem 646 implemented as one or more integrated circuit chips attached to the PCBA 608. Alternatively, the sampling device 100 may be coupled to an external control system, for example one or more programmed general purpose or special purpose computers or computer systems.

The control subsystem 646 may, for example, be coupled to a central communications port 647 (e.g., Universal Serial Bus (USB) or mini-USB compliant female connector) as shown in FIG. 6. The central communications port 647 may be accessible from the exterior of the housing 102, for example via the cable receptacle 504 and the removable access panel 502 in the surface of the housing 102. While illustrated as a hardwired communication port 647 (e.g., a USB port), the sampling device 100 may include other types of communications ports or devices, for instance an infrared transceiver, or an RF transceiver (e.g., BLUETOOTH® transceiver). Such may allow the transmission of data, instructions and/or results, to or from the sampling device 100.

The control subsystem 646 may also include one or more controllers 648, for example, one or more microprocessors, digital signal processors (DSPs), application specific integrated circuits (ASICs), programmable gate arrays (PGA), programmable logic controllers (PLCs), or other logic executing device. The control subsystem may include one or more non-transitory computer- or processor-readable media, for example one or more memories 650 such as read only memory (ROM) 650a, or Flash memory 650b and random access memory (RAM) 650c. One or more buses (not shown) may couple the ROM 650a and RAM 650c to the controller 648. The buses may take a variety of forms including an instruction bus, data bus, other communications bus and/or power bus. A nonvolatile ROM and/or Flash memory 650b may store instructions and/or data for controlling the sampling device 100. The volatile RAM 650c may store instructions and/or data for use during operation of the sampling device 100.

The optional controller 648 can employ instructions and or data from the ROM/Flash 650b and RAM 650c in controlling operation of the sampling device 100. For example, the controller 648 operates the emitters 634 in one or more sequences. The sequences determine an order in which the emitters 634 are turned ON and OFF. The sequences may also indicate an ordered pattern of drive levels (e.g., current levels, voltage levels, duty cycles) for the emitters 634. Thus, for example, a controller 648 may cause the application of different drive levels to respective ones of the emitters 634 to cause the emitters 634 to emit in distinct bands of the electromagnetic spectrum. Thus, the ranges of wavelengths of some of the emitters can be different from the ranges of wavelengths of others of the emitters.

The controller 648 may process information generated by the primary sampling detector(s) or sensor(s) 638, 640, which is indicative of the response by at least a portion of a sample or specimen to illumination by the emitters 634. The information at any given time may be indicative of the response by the sample or specimen to illumination by one or more of the emitters 634. Thus, the information over a period of time may be indicative of the responses by the sample or specimen to sequential illumination by each of a plurality of the emitters 634, where each of the emission spectra of each of the emitters 634 has a different center, bandwidth and/or other more complex differences in spectral content, such as those described above (e.g., width of the band, the skew of the distribution, the kurtosis, etc.). The control subsystem 646 may optionally include a buffer (not shown) to buffer information received from the primary sampling detector(s) or sensor(s). The control subsystem 646 may further optionally include an analog to digital converter (ADC) (not shown) and/or digital to analog converter (DAC) (not shown). An ADC may, for example, be used for converting analog photodiode responses into digital data for further analysis and/or transmission. A DAC may, for example, be used for converting digital computer or controller commands into analog LED current levels. The control subsystem may additionally or alternatively optionally include an analog signal processor, which may be particularly useful where the sensor takes the form of one or more photodiodes.

The control subsystem 646 may include a user interface including one or more user interface devices. For example, the control subsystem 646 may include one or more speakers or microphones (not shown). Also for example, the control subsystem 646 may include and/or one or more visual indicators, such as one or more LEDs, liquid crystal displays (LCD), or other visual indicators, which could include visual indicators 112. The LCD may, for example, take the form of a touch sensitive LCD, which displays a graphical user interface, operable by the user of the sampling device 100.

Additionally, or alternatively, the control subsystem 646 may include one or more user operable input elements, such as switches, keys or buttons, which may include the function buttons 110. The input elements may include a switch for turning the sampling device 100 ON and OFF. Additionally, or alternatively, the input elements may include one or more switches or keys for controlling operation of a test device that can, for example, download or upload data or instructions to, or from the sampling device 100.

Figure 7:
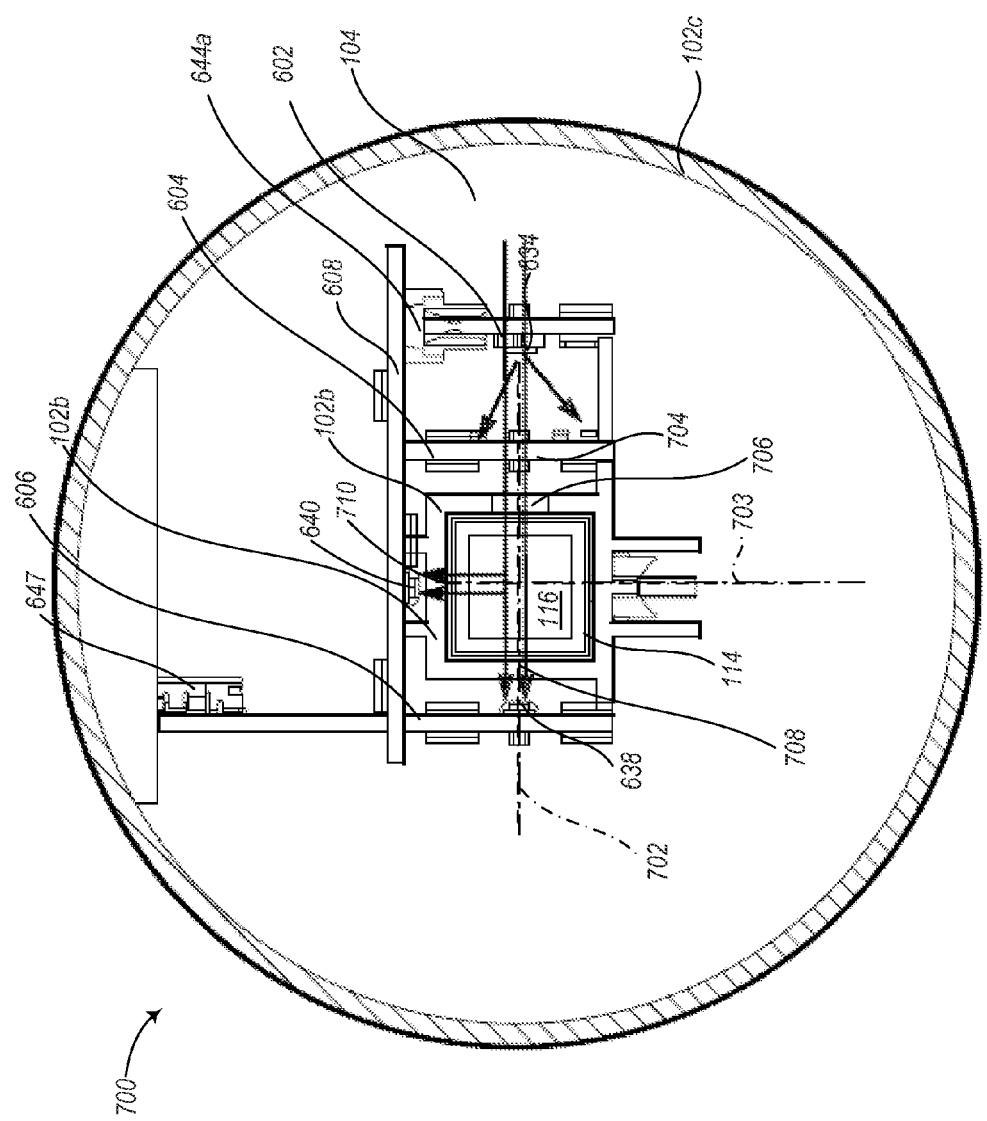
FIG. 7 is a top plan view of the parts assembly of the fluid sampling device of FIG. 6 shown relative to the housing, in which propagation paths of incident and scattered electromagnetic energy are indicated by a ray diagram.

FIG. 7 shows a view 700 of the interior parts shown in FIG. 6, relative to the cap 102c and to the sample chamber 102b. FIG. 7 also shows, from above the sampling device 100, the system geometry, including locations of the emitters 634 and the primary sampling detectors or sensors 638 and 640.

FIG. 7 further includes a ray drawing superimposed onto the view 700, in which arrows indicate transmission paths of electromagnetic energy relative to the interior parts of the sampling device 100. In one embodiment, emitters 634 are selectively operable to emit electromagnetic energy in a respective range of wavelengths through an emission angle that is substantially centered on an optical axis 702. The electromagnetic energy is generally blocked by the calibrator PCBA 604 except where the energy is transmitted through a PCBA slit 704 in the calibrator PCBA 604. The PCBA slit 704 can be substantially aligned with one or more of the emitters 634. Electromagnetic waves admitted through the PCBA slit 704 continue to propagate toward and through a first aperture 706 of the sample chamber 102b and through the transparent walls of the sample cuvette 114. A second aperture 708 of the sample chamber 102b is positioned at least partially across at least a portion of the sample chamber 102b from the first aperture 706. A third aperture 710 of the sample chamber 102b is positioned at least partially across at least a portion of the sample chamber 102b from both the first and the second apertures 706 and 708, respectively. The first, second, and third apertures, 706, 708, and 710 are transmissive of electromagnetic energy of at least some wavelengths in an optical portion of the electromagnetic spectrum, as is the sample cuvette 114.

As the ray drawing indicates, electromagnetic energy strikes the sample or specimen and is scattered and/or reflected therefrom. The scattered electromagnetic waves then emerge from the at least partially transparent walls of the sample cuvette 114, propagating outward in various directions. Again, the electromagnetic energy is generally blocked by the walls of the sample chamber 102b, except where the second aperture 708 permits transmission in the forward scattering direction, along the optical axis 702. The third aperture 710 permits transmission of the scattered energy in a direction perpendicular to the optical axis 702, along a perpendicular axis 703.

After passing through the second aperture 708, a portion of scattered electromagnetic energy propagating along the optical axis 702 falls incident on, and thus can be detected by the first primary sampling detector(s) or sensor(s) 638 mounted on the direct sensor PCBA 606. Similarly, after passing through the third aperture 710, a portion of scattered electromagnetic energy propagating along the perpendicular axis 703 can be detected at one or more of the second primary sampling detector(s) or sensor(s) 640 mounted on the direct sensor PCBA (also the backplane PCBA) 608. In some applications, time varying processes, for example, chemical or biological reactions, can be monitored by detecting the onset of, or change(s) in, "side scatter" along the perndicular axis 703. Onset of such side scatter can indicate, for example, formation of crystals, bacterial growth, formation of blood clots, or other substances in a fluid that can cause electromagnetic energy to be scattered in the direction of the second primary sampling detector(s) or sensor(s) 640. Commensurate with an increase in side scatter along the perpendicular axis 703, there may be observed a decrease in transmission of electromagnetic energy along the optical axis 702. In some instances, such a decrease in transmission intensity and an increase in side scatter intensity can be observed substantially simultaneously (i.e., concurrently) using the sampling device 100. The ability to detect such changes represents a feature of the sampling device 100 that is not provided by other types of sampling devices.

Figure 8:
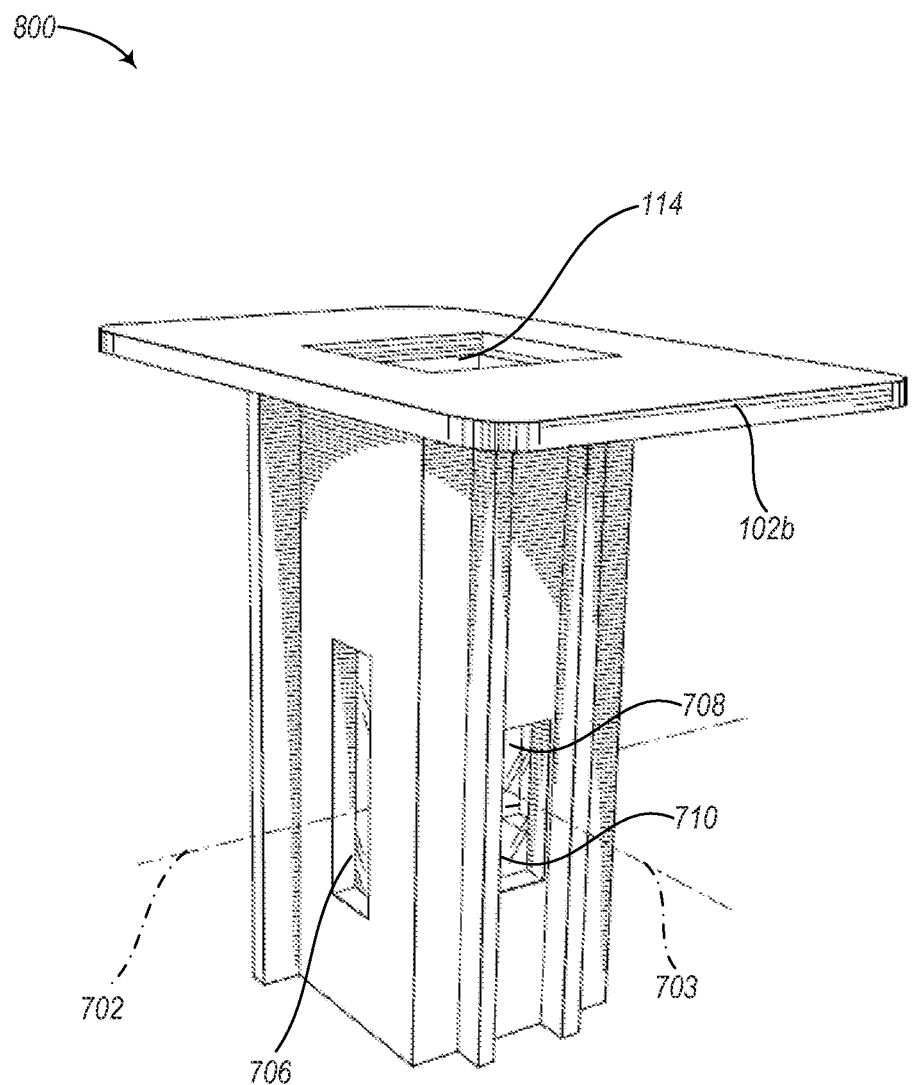
FIG. 8 is a pictorial perspective view of a sample chamber within a fluid sampling device, according to one illustrated embodiment.

FIG. 8 shows a view 800 of the sample chamber 102b. The sample chamber 102b receives and protects the sample cuvette 114 containing the fluid sample under test. The sample cuvette 114 can be inserted at least partially into the center of the sample chamber 102b, which fits closely around the sample cuvette 114. In one embodiment, the sample chamber 102b can be raised and lowered during loading of the sample cuvette. The sample chamber 102b can serve as a double containment receptacle to prevent liquids that may escape the sample cuvette 114 from coming into contact with electronic components of the sampling device 100. The sample chamber 102b can feature a plurality of apertures described above, e.g., the first aperture 706, the second aperture 708, and the third aperture 710, to allow electromagnetic energy to be transmitted to and scattered (or re-emitted) from a sample within the sample cuvette 114. In this way, the sample chamber 102b guides light into the sample cuvette 114. Otherwise, the walls of the sample chamber can be opaque, such that the sample chamber 102b has at least one opaque wall. The first aperture 706 in the sample chamber 102b allows passage of incident electromagnetic energy from one or more of the emitters 634, along the optical axis 702, and through the sample cuvette 114 to interact with the fluid sample. In one embodiment, the second aperture 708 is diametrically opposed to the first aperture 706, allowing passage of scattered electromagnetic energy in the forward direction to exit the sample chamber 102b for detection. The third aperture 710 is disposed along a second axis 703, non-collinear with the optical axis 702. In the embodiment shown, the second axis 703 and the third aperture 710 are oriented perpendicular to the optical axis 702. As illustrated, the first aperture 706 is shown larger than the third aperture 710. However, the relative dimensions of the apertures 706, 708, and 710 can change depending on the type of emitters 634, the nature of the sample, and other variables.

Figure 9:
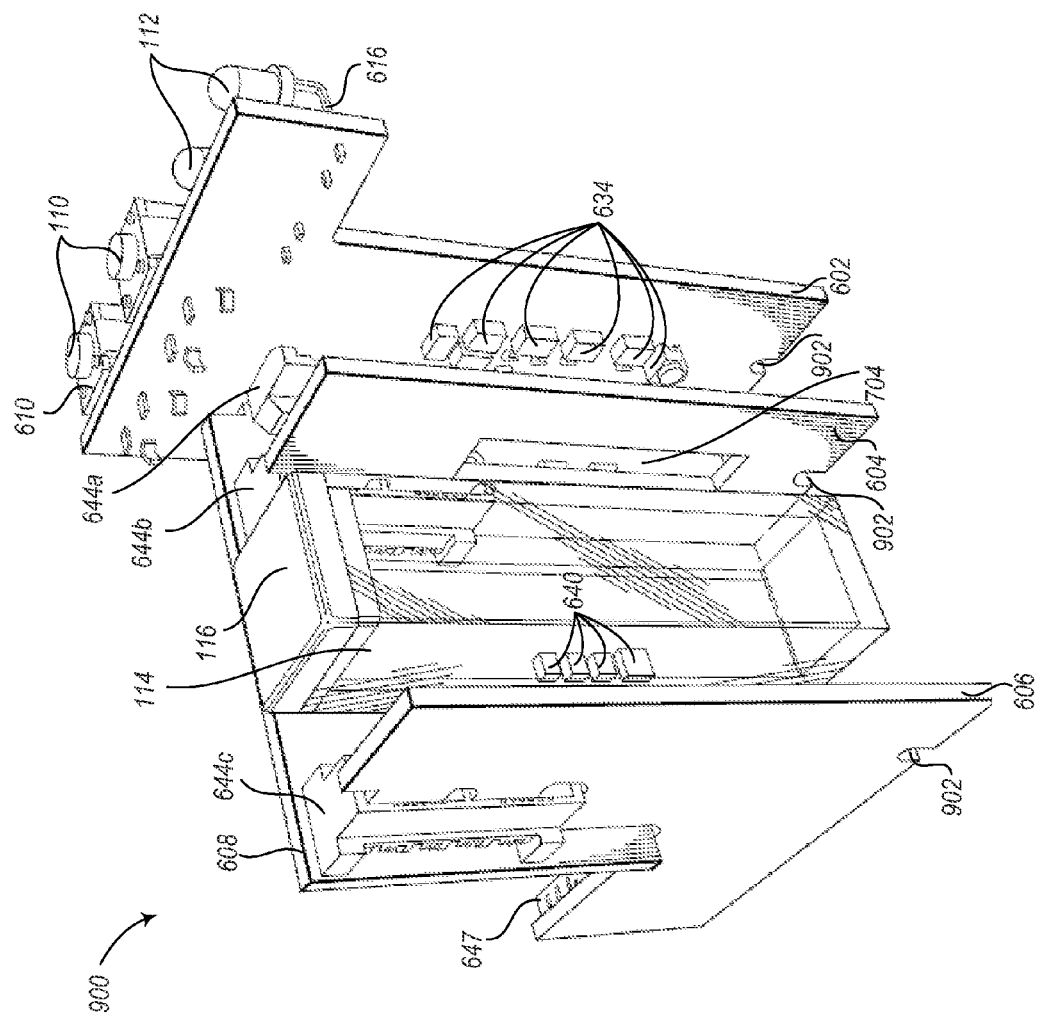
FIG. 9 is an isometric view of the parts assembly of FIG. 6, shown relative to the sample cuvette.

FIG. 9 shows a view 900 of the PCBAs 602, 604, 606, and 608, relative to the sample cuvette 114, in which the calibration sensors 636 and the primary sampling detector(s) or sensor(s) 638, 640 are visible. In an exemplary embodiment, the PCBAs 602, 604, 606, and 608 can attach to the housing 102 by fitting notches 902 onto clips 904 (see FIG. 12). The clips 904 can, in turn, be secured to an interior surface of the base of the housing 106a. When mounted in front of the transducer PCBA 602, the calibrator PCBA 604 serves as a mask in which the PCBA slit 704 allows electromagnetic energy to reach and interact with the fluid sample. The transparent sample cuvette 114 allows electromagnetic energy scattered from the fluid sample to reach the primary sampling detector(s) or sensor(s) 638.

As is best illustrated in FIG. 9, the transducer PCBA 602 carries a number of emitters or sources 634 arranged, for example, in a linear array on the transducer PCBA 602. The emitters 634 may be all aligned with the PCBA slit 704 and the first aperture 706. A full range of emitters can include, for example, 5-10 emitter chips in which each emitter can be made to produce a range of wavelengths of light depending on the electric current supplied to it. Respective ranges of emitters can overlap such that a full range of desired wavelengths can be produced by driving a few emitters at many different current levels. The emitters 634 may take a variety of forms which are operable to emit electromagnetic energy. The emitters 634 may, for example, take the form of one or more light emitting diodes (LEDs), including for instance organic LEDs (OLEDs). Alternatively, or additionally, the emitters 634 may take the form of one or more lasers, for example one or more laser diodes. The lasers may, or may not, be tunable lasers. Alternatively, or additionally, the emitters 634 may take the form of one or more incandescent sources such as conventional or halogen light bulbs.

One, more, or all of the emitters 634 may be operable to emit in part or all of an "optical" portion of the electromagnetic spectrum, including the (human) visible portion, near infrared (N-IR) portion and/or or near ultraviolet (N-UV) portions of the electromagnetic spectrum. Additionally, or alternatively, the emitters 634 may be operable to emit electromagnetic energy other portions of the electromagnetic spectrum, for example the infrared, ultraviolet and/or microwave portions.

In some embodiments, at least some of the emitters 634 are operable to emit in or at a different band than other of the emitters 634. For example, one or more emitters 634 may emit in a band centered around 450 nm, while one or more of the emitters 634 may emit in a band centered around 500 nm, while a further emitter or emitters emit in a band centered around 550 nm. Each of the emitters 634 may emit in a band centered around a respective frequency or wavelength, different than each of the other emitters 634. Using emitters 634 with different band centers advantageously maximizes the number of distinct samples that may be captured from a fixed number of emitters 634. This may be particularly advantageous where the sampling device 100 is relatively small, and has limited space or footprint for the emitters 634.

The distribution of spectral content for each emitter 634 may vary as a function of drive level (e.g., current, voltage, duty cycle), temperature, and other environmental factors, depending on the specific emitter 634. Such variation may be advantageously actively employed to operate one or more of the physical emitters 634 as a plurality of "logical emitters or sources," each of the logical emitters or sources operable to provide a respective emission spectra from a respective physical emitters or source 634. Thus, for example, the center of the band of emission for each emitters or source 634 may vary according to a drive level and/or temperature. For example, the center of the band of emission for LEDs will vary with drive current or temperature. One way the spectral content can vary is that the peak wavelength can shift. However, the width of the band, the skew of the distribution, the kurtosis, etc., can also vary. Such variations may be also be advantageously employed to operate the physical emitters or sources 634 as a plurality of logical emitters or sources. Thus, even if the peak wavelength were to remain constant, the changes in bandwidth, skew, kurtosis, and any other change in the spectrum can provide useful variations in the operation of the sampling device 100. Likewise, the center of the band of emission may be varied for tunable lasers. Varying the center of emission bands for one or more emitters 634 advantageously maximizes the number of samples that may be captured from a fixed number of emitters 634. Again, this may be particularly advantageous where the sampling device 100 is relatively small, and has limited space or footprint for the emitters 634.

Figure 10:
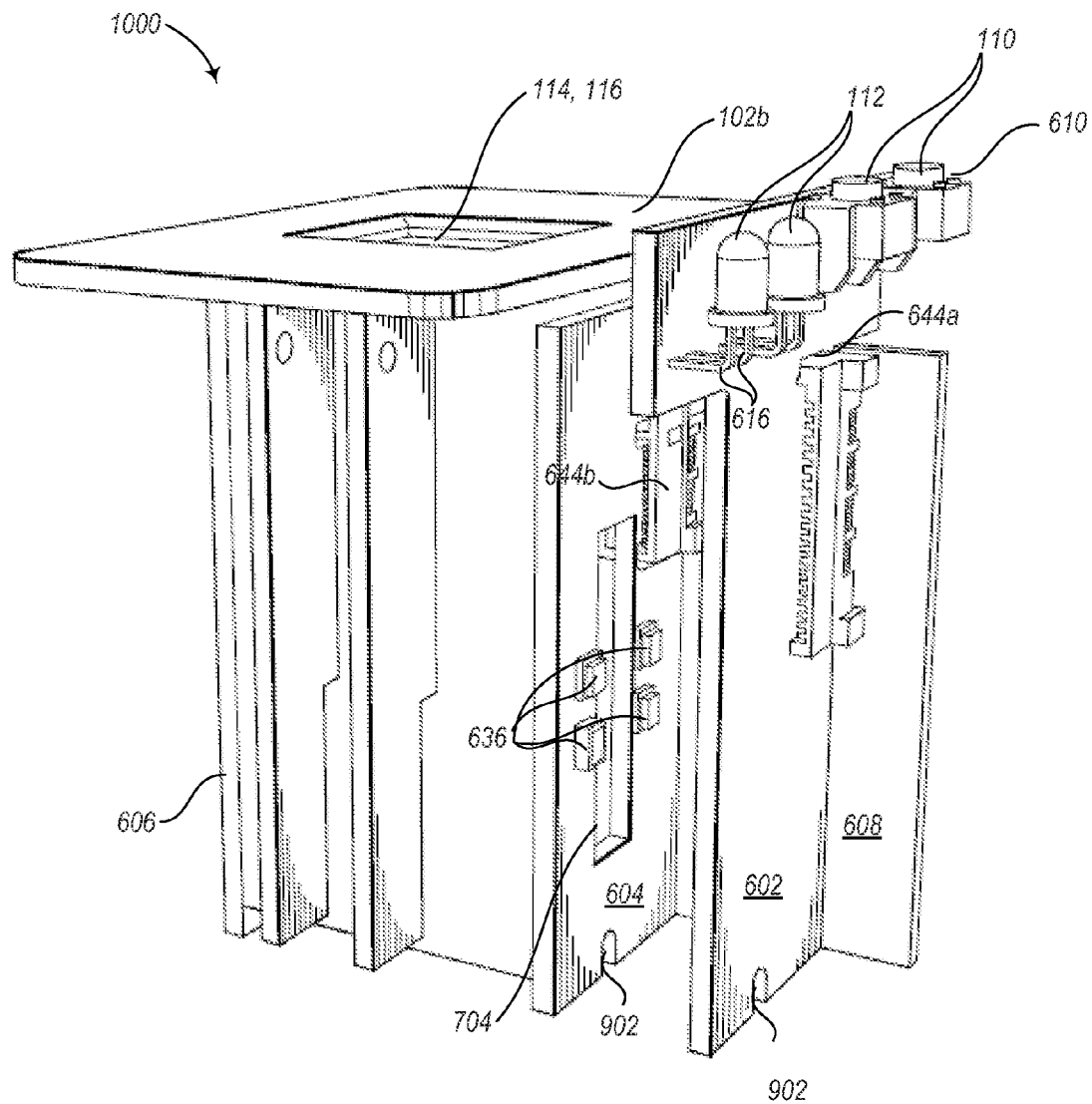
FIG. 10 is an isometric view of the parts assembly shown in FIG. 9, relative to the sample chamber, according to one illustrated embodiment.

As is best illustrated in FIG. 10, the calibration PCBA 604 carries a number of calibration detectors or sensors (four shown, collectively 636), arranged around the PCBA slit 704. The number of calibration detectors or sensors 636 can correspond to the number of emitters 634. The calibration detectors or sensors 636 are generally aligned with respective emitters 634, the calibration detectors or sensors 636 and emitters 634 for example being arranged in linear segments on a surface of the calibration PCBA 604. The calibration detectors or sensors 636 may match a nominal output of the respective emitter 634 to which the calibration detector or sensor 636 is paired. Thus, some of the calibration detectors or sensors 636 may be responsive to different respective bands of wavelengths than the others. Such bands may be mutually exclusive or may be overlapping. Some embodiments employ one or more wideband calibration detectors or sensors 636, for example, a pyroelectric detector from Pyreos Ltd. Such may advantageously reduce parts counts, while still allowing calibration across the range of wavelengths of the emitters 634. Optionally, one or more filters (not shown) may be employed with the calibration detectors or sensors 636, for example one or more low pass filters, high pass filters, and/or band pass filters. The filters may be optical filters and may be formed or carried directly on the calibration detectors or sensors 636. Alternatively, the filters may be formed on or carried on another surface, in the field of view of but spaced from the calibration detectors or sensors 636.

The calibration detector(s) or sensor(s) 636 can take a variety of forms suitable for sensing or responding to electromagnetic energy. For example, the calibration detector(s) or sensor(s) 636 may take the form of one or more photodiodes (e.g., germanium photodiodes, silicon photodiodes). Alternatively, or additionally, the calibration detector(s) or sensor(s) 636 may take the form of one or more photomultiplier tubes. Alternatively, or additionally, the calibration detector(s) or sensor(s) 636 may take the form of one or more CMOS image sensors. Alternatively, or additionally, the calibration detector(s) or sensor(s) 636 may take the form of one or more charge coupled devices (CCDs). Alternatively, or additionally the calibration detector(s) or sensor(s) 636 may take the form of one or more microchannel plates. Other forms of electromagnetic sensors may be employed, which are suitable to detect the wavelengths expected to be returned in response to the particular illumination and properties of the object being illuminated.

The calibration detector(s) or sensor(s) 636 may be formed as individual elements, one-dimensional array of elements and/or two-dimensional array of elements. For example, the calibration detector(s) or sensor(s) 636 may be formed by one germanium photodiode and one silicon photodiode, each having differing spectral sensitivities. A test device may employ a number of photodiodes with identical spectral sensitivities, with different colored filters (e.g., gel filters, dichroic filters, thin-film filters, etc) over the photodiodes to change their spectral sensitivity. This may provide a simple, low-cost approach for creating a set of sensors with different spectral sensitivities, particularly since germanium photodiodes are currently significantly more expensive that silicon photodiodes. Also for example, the calibration detector(s) or sensor(s) 636 may be formed from one CCD array (one-dimensional or two-dimensional) and one or more photodiodes (e.g., germanium photodiodes and/or silicon photodiodes). For example, the calibration detector(s) or sensor(s) 636 may be formed as a one- or two-dimensional array of photodiodes. A two-dimensional array of photodiodes enables very fast capture rate (i.e., camera speed) and may be particularly suited to use in assembly lines or high speed sorting operations. For example, the calibration detector(s) or sensor(s) 636 may be formed as a one- or two-dimensional array of photomultipliers. Combinations of the above elements may also be employed.

In some embodiments, the calibration detector(s) or sensor(s) 636 may be a broadband sensor sensitive or responsive over a broad band of wavelengths of electromagnetic energy. In some embodiments, the calibration detector(s) or sensor(s) 636 may be narrowband sensors sensitive or responsive over a narrow band of wavelengths of electromagnetic energy. In some embodiments, the calibration detector(s) or sensor(s) 636 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

Figure 11:
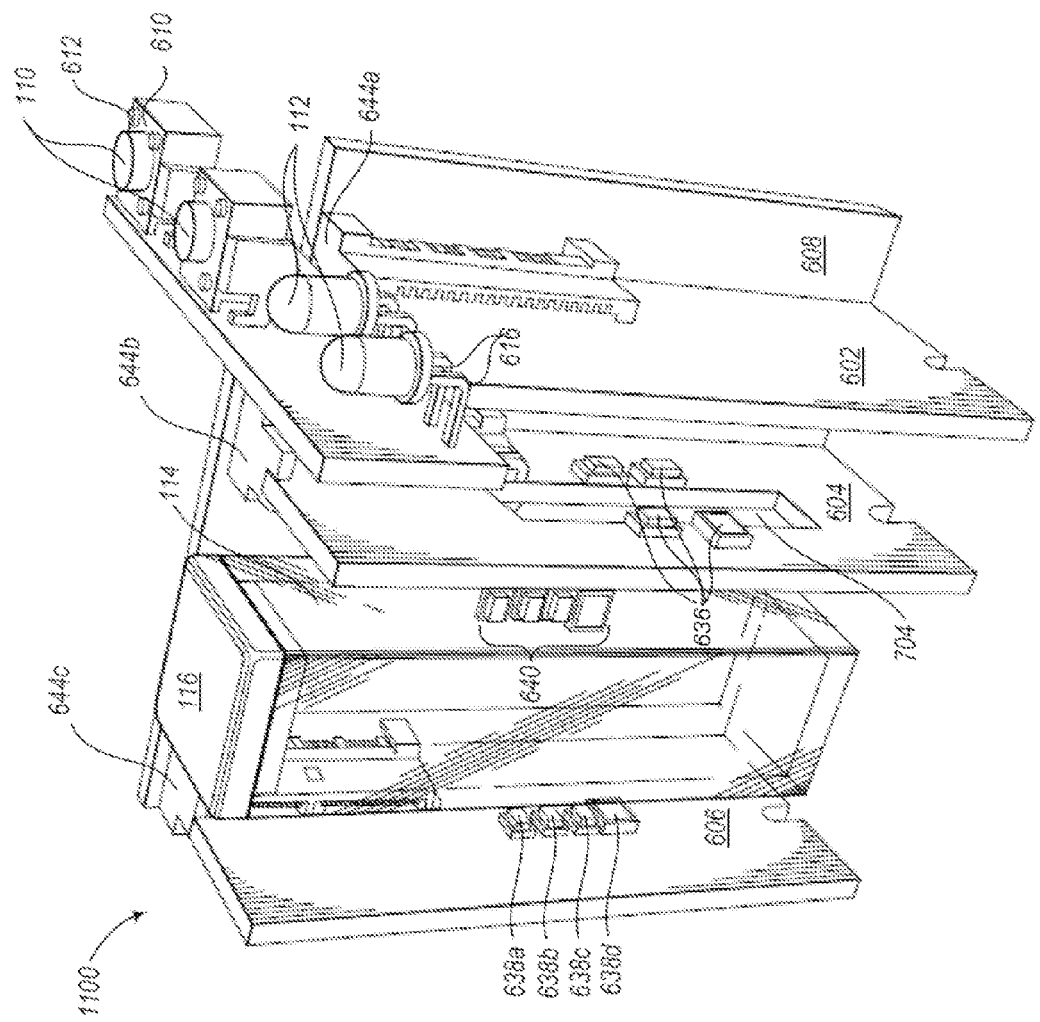
FIG. 11 is an isometric view of the parts assembly of the fluid sampling device of FIG. 6, shown relative to the sample cuvette, in which emitter chips are shown mounted on the emitter printed circuit board assembly and sensor chips are shown on the backplane.

As is best illustrated in FIG. 11, the direct sensor PCBA 606 carries a number of first primary sampling sensors 638a-638d (four shown, collectively 638) positioned opposite the PCBA slit 704. The first primary sampling sensors 638 may, for example, include two or more sampling sensors or detectors, each responsive to a respective band of wavelengths. Such bands may be mutually exclusive or overlapping. The illustrated embodiment employs four first primary sampling detectors or sensors 638a-638d, each responsive to a respective band of wavelengths (i.e., 400 nm-1100 nm, 400 nm-1050 nm, 400 nm-1050 nm, 600 nm-1700 nm, respectively). Three of the first primary sampling detectors or sensors 638a-638c that are responsive to N-UV wavelengths are employed to increase to sensitivity. Another embodiment employs one or more wideband first primary sampling detector(s) or sensor(s) 638d, for example, a pyroelectric detector from Pyreos Ltd. Optionally, one or more filters (not shown) may be employed with the first primary sampling detector(s) or sensor(s) 638, for example one or more low pass filters, high pass filters, and/or band pass filters. The filters may be optical filters and may be formed or carried directly on the first primary sampling detector(s) or sensor (s). Alternatively, the filters may be formed on or carried on another surface, in the field of view of but spaced from the first primary sampling sampling detector(s) or sensor(s) 638.

The first primary sampling detector(s) or sensor(s) 638, or spectrophotometers, can take a variety of forms suitable for sensing or responding to electromagnetic energy. For example, the primary sampling sensor(s) 638 may take the form of one or more photodiodes (e.g., germanium photodiodes, silicon photodiodes). Alternatively, or additionally, the primary sampling detector(s) or sensor(s) 638 may take the form of one or more photomultiplier tubes. Alternatively, or additionally, the first primary sampling detector(s) or sensor(s) 638 may take the form of one or more CMOS image sensors. Alternatively, or additionally, the first primary sampling detector(s) or sensor(s) 638 may take the form of one or more charge coupled devices (CCDs). Alternatively, or additionally the first primary sampling detector(s) or sensor(s) 638 may take the form of one or more micro-channel plates. Other forms of electromagnetic sensors may be employed, which are suitable to detect the wavelengths expected to be returned in response to the particular illumination and properties of the object being illuminated.

The first primary sampling detector(s) or sensor(s) 638 may be formed as individual elements, one-dimensional array of elements and/or two-dimensional array of elements. For example, the first primary sampling detector(s) or sensor (s) 638 may be formed by one germanium photodiode and one silicon photodiode, each having differing spectral sensitivities. A test device can be configured with a number of photodiodes having identical spectral sensitivities, with different colored filters (e.g., gel filters, dichroic filters, thin-film filters, etc.) over the photodiodes to change their spectral sensitivity. This may provide a simple, low-cost approach for creating a set of sensors with different spectral sensitivities, particularly since germanium photodiodes are currently significantly more expensive that silicon photodiodes. Also for example, the first primary sampling detector (s) or sensor(s) 638 may be formed from one CCD array (one-dimensional or two-dimensional) and one or more photodiodes (e.g., germanium photodiodes and/or silicon photodiodes). For example, the first primary sampling detector(s) or sensor(s) 638 may be formed as a one- or two-dimensional array of photodiodes. A two-dimensional array of photodiodes enables very fast capture rate (i.e., camera speed) and may be particularly suited to use in assembly lines or high speed sorting operations. For example, the first primary sampling detector(s) or sensor(s) 638 may be formed as a one- or two-dimensional array of photomultipliers. Combinations of the above elements may also be employed.

In some embodiments, the primary sampling detector(s) or sensor(s) 638, 640 may be a broadband sensor sensitive or responsive over a broad band of wavelengths of electromagnetic energy. In some embodiments, the primary sampling detector(s) or sensor(s) 638, 640 may be narrowband sensors sensitive or responsive over a narrow band of wavelengths of electromagnetic energy. In some embodiments, the primary sampling detector(s) or sensor(s) 638, 640 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

At least one of the PCBAs 602, 604, 606, and 608 can also carry one or more thermal sensors (not explicitly shown). The thermal sensors are desirably distributed to detect temperature at a variety of points or locations. Such temperatures may be indicative of temperatures to which the emitters 634, first primary sampling detectors or sensors 638 and/or calibration detectors or sensors 636 are subjected. Temperature indicative signals from the thermal sensors may be employed in calibration, for example, calibrating results or responses and/or calibrating drive signals to account from variation from nominal temperatures or other conditions.

Table A, below, provides an exemplary list of suitable parts for the emitters and sensors. Such is purely illustrative and is not intended to require any specific parts, specific wavelengths, or sensitivities.

TABLE A

| Ref. No. | Part No. | Description | Default/Qty. |
| --- | --- | --- | --- |
| 606 | Max2 Sensor PCBA | PCBA | 1 |
| — | MCP98242 | Thermal Sensor | 4 |
| 644a | HSEC8-120-01-X-DV | Connector | 1 |
| 634a | 350-PLCC2-120 | 352 nm | 1 |
| 634b | SM1206UV-395-IL | 400 nm | 1 |
| 634c | EL-19-21/BHC-AN1P2/3T | 468 nm | 1 |
| 634d | PG1112C-TR | 567 nm | 1 |
| 634e | LTST-C190KYKT | 595 nm | 1 |
| 634f | SMC810 | 810 nm | 1 |
| 634g | SMC1200 | 1200 nm | 1 |
| 634h | LNJ812R83RA | 630 nm | 1 |
| 634i | SMC1450 | 1450 nm | 1 |
| 634j | SMC910 | 910 nm | 1 |
| 634k | LN1251CTR | 700 nm | 1 |
| 634l | SMC970 | 970 nm | 1 |
| 636a | PDB-C152SM | 400-1100 nm | 1 |
| 636b | SFH2701 | 400-1050 nm | 1 |
| 636c | PDB-C152SM | 400-1100 nm | 1 |
| 636d | LAPD-1-06-17-LCC | 600-1700 nm | 1 |
| 638a | SFH2701 | 400-1050 nm | 1 |
| 638b | SFH2701 | 400-1050 nm | 1 |
| 638c | PDB-C152SM | 400-1100 nm | 1 |
| 638d | PDB-C152SM | 400-1100 nm | 1 |
| 638e | PDB-C152SM | 400-1100 nm | 1 |
| 638f | PDB-C152SM | 400-1100 nm | 1 |
| 638g | LAPD-1-06-17-LCC | 600-1700 nm | 1 |
| 638h | PDB-C152SM | 400-1100 nm | 1 |
| 638i | LAPD-1-06-17-LCC | 600-1700 nm | 1 |
| 638j | PDB-C152SM | 400-1100 nm | 1 |
| 638k | PDB-C152SM | 400-1100 nm | 1 |
| 638l | PDB-C152SM | 400-1100 nm | 1 |

By commonly housing emitters 634 with respective calibration detector(s) or sensor(s) 636 or sensors 638, the sampling device may automatically take or capture an electromagnetic energy calibration sample or measurement each time an emitter emits electromagnetic energy. Such is performed in real-time, without any separate calibration mode. Such may be performed individually for each emitter, one at a time, as the emitter is activated. Thermal sensors 635 may be sampled each time an emitter is activated. Alternatively, the thermal sensors 635 may be sampled periodically or aperiodically. The electromagnetic energy calibration sample or measurements and thermal calibration sample or measurements may be used to calibrate a detected or measured response. The electromagnetic energy calibration sample or measurements and thermal calibration sample or measurements may additionally or alternatively be used to control operation, for instance to control a drive signal supplied to the emitters, or control an amplification applied to a signal produced or provided by the first primary sampling detectors or sensors 638. As discussed below, the electromagnetic energy calibration sample or measurements and thermal calibration sample or measurements may be processed on the sampling device 100, or sent to a separate component (e.g., digital computer) for processing.

While FIGS. 9-11 show seven emitters 634, four calibration detector(s) or sensor(s) 636 and eight primary sampling detectors or sensors 638, 640, other embodiments may include fewer or greater number of emitters 634, and calibration detector(s) or sensor(s) 636 or primary sampling detector(s) or sensor(s) 638, 640. The total number of emitters 634, calibration detector(s) or sensor(s) 636, and primary sampling detector(s) or sensor(s) 638, 640, should not be considered limiting.

Figure 12:
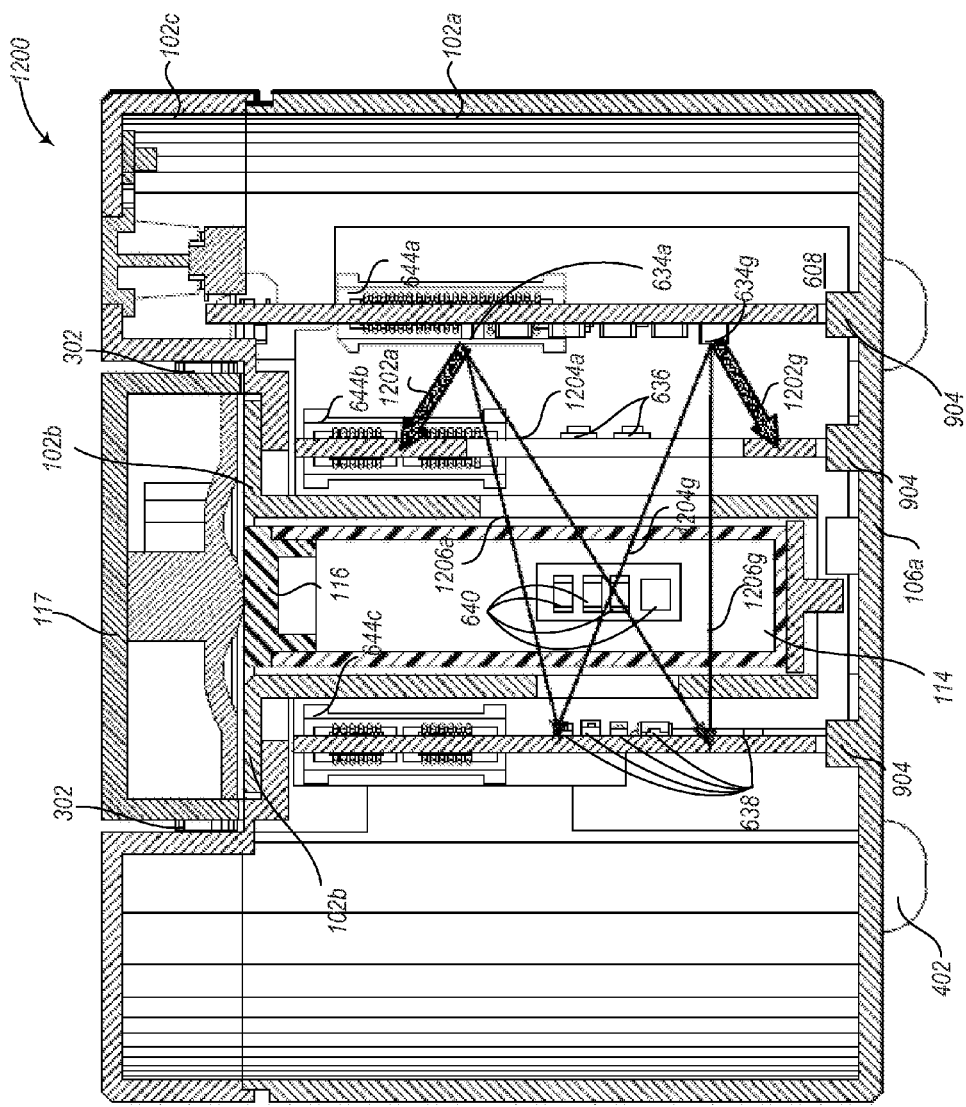
FIG. 12 is an interior side elevation view of one embodiment of a fluid sampling device, in which propagation paths of incident and scattered electromagnetic energy are indicated.

FIG. 12 shows a view 1200 of the sampling device 100 as seen from the rear. Internal parts are shown relative to overall structural components such as the main body housing portion 102a, the cap 102c, the hinged lid 117, and the sample chamber 102b. Superimposed onto the structure of the sampling device 100 is a side view of a ray diagram similar to that shown in FIG. 7. In the view 1200, electromagnetic energy is shown being emitted through a wide range of angles from the exemplary top and bottom emitters 634a and 634g. The diameter of the emitted beam may depend on the nature of the emitter. The outermost rays 1202a and 1202g, emanating from the emitters 634a and 634g, respectively, fail to pass through the PCBA slit 704 (not shown) and therefore do not interact with the sample. If the emitters 634 are laser sources, for example, the outermost rays may not be relevant because laser sources produce a collimated beam. (However, even a collimated beam may exhibit spreading.) In general, a portion of the energy emitted can be expected to escape the system without encountering the sample under test. The innermost rays emitted, 1204a and 1204g, respectively, are shown crossing at the center of the sample cuvette 114, in front of the second primary sampling detector(s) or sensor(s) 640, which are attached to the backplane 608. The innermost rays therefore interact with substantially the same part of the sample contained in the sample cuvette 114. It is noted that the innermost rays shown have different wavelengths because they originate at different sources. A portion of the electromagnetic energy in the innermost rays 1204a and 1204g is scattered by the sample. Some of the scattered energy is shown continuing to propagate in the forward direction for detection by the sensors 638. Thus, comparing the energy scattered by the same sample at multiple wavelengths permits identification of a localized portion of the sample. Meanwhile, the central rays 1206a and 1206g, from the two different emitters 634a and 634g, respectively, interact with different portions of the fluid sample. The central rays are also scattered, and a portion of this scattered energy propagates to the detectors 638. By comparing the scattered energy from the central rays 1206a and 1206g with that from the innermost rays 1204a and 1204g, information about the homogeneity of the sample can be obtained. For example, particles suspended in the fluid can be identified and distinguished from the fluid itself.

Figure 13:
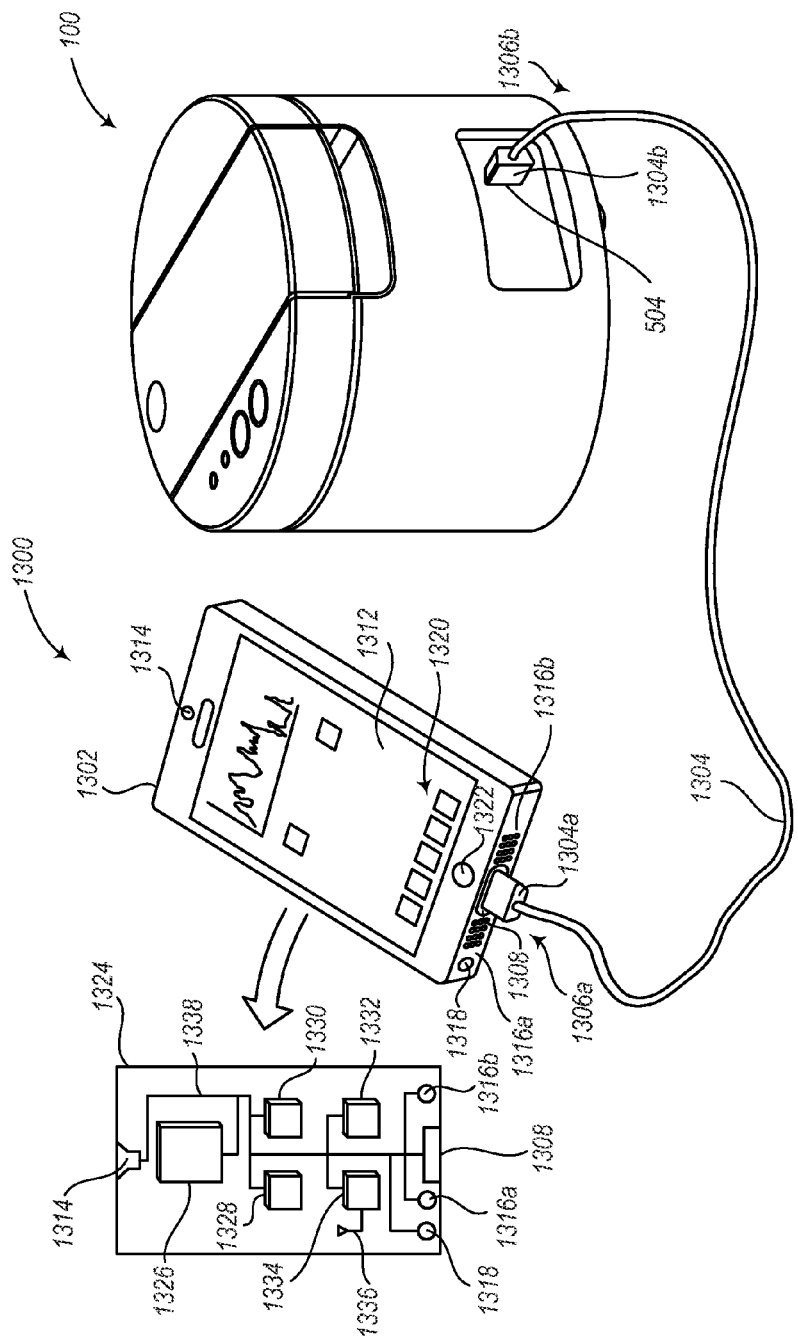
FIG. 13 is an isometric view of a sampling system that includes one or more fluid sampling devices and one or more processor-based devices to which the fluid sampling devices are communicatively coupled, according to one illustrated embodiment.

FIG. 13 shows a sampling system 1300, according to one illustrated embodiment. The sampling system 1300 includes one or more sampling devices 100 (one shown). The sampling system 1300 includes one or more processor-based devices 1302 (one shown). While illustrated as a mobile or handheld processor-based device 1302, for instance a Smartphone type device, the processor-based device 1302 may take a large variety of other forms. For example, the mobile or handheld processor-based device 1302 may take the form of the various computers or computing systems, such as a desktop or laptop personal computer, tablet computer, netbook computer, mini-computer, mainframe computer, or server computer.

The sampling device 100 is communicatively coupled to the processor-based device 1302.

The sampling device 100 may be communicatively coupled to the processor-based device 1302 via a physical communicative path such as a cable 1304.

The cable 1304 will typically include a connector proximate at least one end thereof, and often at both ends. For example, the cable 1304 may have a first connector 1304a (e.g., plug) at a first end 1306a, the first connector 1304a selectively detachably coupleable to a complimentary connector or port 1308 on the processor-based device 1302. Also for example, the cable 1304 may have a second connector 1304b (e.g., plug) at a second end 1306b, the second connector 1304b selectively detachably coupleable to a complimentary connector or port on the sampling device 100 such as the cable receptacle 504. Alternatively, the second end of the cable 1304 may be permanently fixed to the sampling device 100. The physical ports and/or connectors 1304a, 1304b, 1308, 504 and/or cables 1304 may comply with any variety of physical and/or logical standards, and may incorporate one or more integrated circuits. For instance, the ports and/or connectors 1304a, 1304b, 1308, 504 and/or cables 1304 may comply with standards required of USB® standards or Apple Computer's Lighting® standards.

The cable 1304 may, for instance, include a number of distinct electrical conductors (e.g., wires) (not shown) to provide signals between the sampling device 100 from the processor-based device 1302. The electrical conductors may provide for bi-directional communications between the sampling device 100 and the processor-based device 1302. The cable 1304 may additionally provide electrical power (e.g., 5V, 10V) to the sampling device 100 from the processor-based device 1302. In such an implementation, the sampling device 100 may omit any on-board consumable power source (e.g., primary or secondary chemical battery, ultra-capacitor, fuel cell) (not shown). Alternatively, the sampling device 100 may include a recharging circuit (not shown) that uses electrical power supplied via the cable 1304 to recharge an onboard power source (e.g., secondary chemical battery, ultra-capacitor, fuel cell) (not shown).

The cable 1304 may include one or more optical paths (e.g., optical fibers) (not shown). The optical paths may provide for bi-directional communications between the sampling device 100 and the processor-based device 1302.

The sampling device 100 may be communicatively coupled to the processor-based device 1302 via a wireless (e.g., radio frequency, microwave, visible or IR light) communicative path. As discussed below, many processor-based devices 1302 include various radios or receivers, including ones that are compliant with cellular (e.g., CDMA, GSM, LTE), BLUETOOTH or WI-FI protocols. In such implementations, the sampling device 100 may include one or more radios or transceivers (not shown) can be implemented as one or more integrated circuits and/or antennas (not shown). The integrated circuits and/or antennas (not shown) may be carried by the backplane PCBA 608 or some other PCBA, for instance a dedicated communications PCBA (not shown). In such implementations, the sampling device 100 will typically require an on-board consumable power source (e.g., primary or secondary chemical battery, ultra-capacitor, fuel cell) (not shown).

The sampling device 100 may be communicatively coupled via one or more networks (not shown) to various processor-based devices 1302 and/or other sampling devices 100. The network(s) may take a variety of forms including LANs, WANs, WLANs, WWANs, PSTN, to name a few. Such may, for example allow access to one or more storage or databases of information. Such may, for example allow updating or reconfiguration, for instance by downloading of processor-executable instructions. Such may, for example, allow troubleshooting of the sampling device 100 should an error condition occur.

The processor-based device 1302 may include a user interface which may, for example include a touch-sensitive display 1312, speakers 1314 (one shown), microphones 1316a, 1316b (collectively 1316), and/or an audio output port 1318. The user interface may also include user selectable icons, collectively 1320, and/or one or more physical switches, keys or buttons 1322.

FIG. 13 further illustrates a PCBA 1324 of the processor-based device 1302, removed therefrom to better illustrate various components housed within a housing of the processor-based device 1302. The processor-based device 1302 includes one or more processors, for instance a microprocessor 1326. The processor-based device 1302 includes one or more non-transitory computer- or processor-readable media, for instance ROM or Flash 1328 and/or RAM 1330.

Referring to FIG. 13, the microprocessor 1326 employs instructions and or data from the ROM/Flash 1328 and/or RAM 1330 in controlling operation of the sampling device 100. For example, the processor 1326 operates the emitters 634 in one or more sequences. The sequences determine an order in which the emitters 634 are turned ON and OFF. The sequences may also indicate an ordered pattern of drive levels (e.g., current levels, voltage levels, duty cycles) for the emitters 634. Thus, for example, the processor 1326 may cause the application of different drive levels to respective ones of the emitters 634 to cause the emitters 634 to emit in distinct bands of the electromagnetic spectrum. The processor 1326 may process information generated by the first primary sampling detector(s) or sensor(s) 638, which is indicative of the response by at least a portion of a sample or specimen to illumination by the emitters 634. The information at any given time may be indicative of the response by the sample or specimen to illumination by one or more of the emitters 634. Thus, the information over a period of time may be indicative of the responses by the sample or specimen to sequential illumination by each of a plurality of the emitters 634, where each of the emission spectra of each of the emitters 634 has a different center, bandwidth and/or other more complex differences in spectral content, such as those described above (e.g., width of the band, the skew of the distribution, the kurtosis, etc.).

The processor 1326 employs instructions and or data from the ROM/Flash 1328 and RAM 1330 to perform analysis or evaluation of the responses. For example, the processor 1326 may compare a response to one or more reference responses. The processor 1326 may determine whether a response from a sample or specimen sufficiently matches is signature responses from a reference sample or specimen. Such may, for example, be employed to detect a presence or absence of a substance, for instance an illegal substance (e.g., cocaine), an explosive substance (e.g., nitrate based), or a toxic substance (e.g., carcinogens). The processor 1326 may cause display of a result of an analysis or evaluation. For instance, the processor 1326 may cause display of a simple indicator (e.g., check, YES/NO, other text, GREEN/RED/AMBER or other color) indicative of the result. Also for instance, the processor 1326 may cause display of a more complex indicator (e.g., graph, table chart) indicative of the result. Additionally or alternatively, the processor 1326 may cause an aural indication indicative of a result via speaker 1314, for example a sound such as a beep, buzz, or even spoken or synthesized words.

The processor-based device 1302 may additionally include a display driver 1332, communicatively coupled to drive the touch-sensitive display 1312 and/or detect touches, swipes or other user inputs via the touch-sensitive display 1312. The display driver 1332 may be a dedicated integrated circuit, for example a graphical processing unit.

The processor-based device 1302 may additionally include one or more radios or transceivers 1334 (only one shown) and one or more associated antennas 1336 (only one shown). The radios or transceivers 1334 and antennas 1336 may take any of a large variety of forms, for example ones suitable for wireless communications such as cellular communications (e.g., CDMA, GSM, LTE), BLUETOOTH communications and/or WI-FI communications.

The processor-based device 1302 may additionally include one or more accelerometers or gyroscopes. Such components may be capable of producing data indicative of an orientation of the processor-based device 1302. Such components may be capable of producing data indicative of a speed, movement or acceleration of the processor-based device 1302.

The various components may be communicatively coupled via one or more buses 1338 (only one shown) or other connections, for example data buses, instruction buses, address buses, power buses, etc.

As used herein and in the claims, longitudinal refers to the major dimension or length of a structure, and is not limited to being an axis of revolution of a profile or cross-section of such structure.

As used herein and in the claims, the term "non-transitory computer-readable medium" and "non-transitory processor-readable medium" are used interchangeably to refer to any tangible medium that participates in providing instructions for execution or storage of data, parameters or other information. Such a medium may take many forms, including but not limited to, non-volatile media and volatile media. Non-volatile media includes, for example, hard, optical or magnetic disks. Volatile media includes dynamic memory, such as system memory. Common forms of computer- or processor-readable media include, for example, floppy disk, flexible disk, hard disk, magnetic tape, or any other magnetic medium, CD-ROM, any other optical medium, punch cards, paper tape, any other physical medium with patterns of holes, RAM, PROM, EPROM, EEPROM, FLASH memory, any other memory chip or cartridge, or any other tangible medium from which a computer or processor can read.

While not illustrated, the sampling device 100 may include one or more elements operable to deflect or otherwise position the emitted or received electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, for example permanent magnets or electromagnets such as those associated with cathode ray tubes and/or mass spectrometers.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to: U.S. Pat. Nos. 7,996,173; 8,081,304; and 8,076, 630; U.S. Provisional Patent Application Ser. Nos.: 61/760, 527, filed Feb. 4, 2013; 60/623,881, filed Nov. 1, 2004; 60/732,163, filed Oct. 31, 2005; 60/820,938, filed Jul. 31, 2006; 60/834,662, filed Jul. 31, 2006; 60/834,589, filed Jul. 31, 2006; 60/871,639, filed Dec. 22, 2006; 60/883,312, filed Jan. 3, 2007; 60/890,446, filed Feb. 16, 2007; 61/538,617, filed Sep. 23, 2011; 61/760,527, filed Feb. 4, 2013; 61/597, 586, filed Feb. 10, 2012; 61/597,593, filed Feb. 10, 2012; 61/767,716, filed Feb. 21, 2013; and 13/797,737, filed Mar. 12, 2013 are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sampling device, comprising:
a sample chamber, the sample chamber having an interior to receive a sample cuvette at least partially therein, the sample chamber having at least one opaque wall, a first aperture, a second aperture positioned diametrically across the sample chamber from the first aperture, and a third aperture positioned along an axis perpendicular to an optical axis that extends between the first and the second apertures, the first, the second, and the third apertures transmissive of electromagnetic energy of at least some wavelengths in an optical portion of the electromagnetic spectrum;
an emitter circuit board, the emitter circuit board spaced from the sample chamber opposed to the first aperture of the sample chamber, the emitter circuit board carrying a plurality of emitters, each of the emitters selectively operable to emit electromagnetic energy in a respective range of wavelengths toward the first aperture of the sample chamber, the ranges of wavelengths of at least some of the emitters different from the ranges of wavelengths of others of the emitters;
a calibration circuit board spaced outwardly of the sample chamber and positioned between the sample chamber and the emitter circuit board, the calibration circuit board having a first face opposed to the first aperture of the sample chamber, a second face opposite the first face, and a slit that is transmissive of electromagnetic energy of at least some wavelengths in the optical portion of the electromagnetic spectrum, the calibration circuit board having at least one calibration sensor affixed to the second face of the calibration circuit board to face the emitter circuit board to receive electromagnetic energy emitted by at least one of the emitters, substantially free of electromagnetic energy emitting, if any, from the sample chamber;
a direct sensor circuit board spaced outwardly of the sample chamber opposed to the second aperture of the sample chamber, the direct sensor circuit board having at least one primary sampling sensor positioned to receive electromagnetic energy emitting from the sample chamber via the second aperture; and
an indirect sensor circuit board spaced outwardly of the sample chamber opposed to the third aperture, the indirect sensor circuit board perpendicular to the direct sensor circuit board, the indirect sensor circuit board carrying a number of second primary sampling sensors positioned to receive electromagnetic energy indirectly scattered from the sample chamber along an axis that is perpendicular to the optical axis that extends between the first and the second apertures.

2. The sampling device of claim 1, wherein the indirect sensor circuit board is perpendicular to the calibration circuit board.

3. The sampling device of claim 2, wherein the emitter circuit board is parallel to the calibration circuit board.

4. The sampling device of claim 1, wherein the emitter circuit board is parallel to the calibration circuit board.

5. The sampling device of claim 1, wherein the calibration circuit board is parallel to the direct sensor circuit board.

6. The sampling device of claim 5, wherein the emitter circuit board is parallel to the calibration circuit board.

7. The sampling device of claim 1, wherein the at least one calibration sensor includes at least a first calibration sensor positioned to one side of the slit and at least a second calibration sensor positioned to another side of the slit, the other side of the slit disposed across the slit from the first side of the slit.

8. The sampling device of claim 7, wherein the emitters are all aligned with the slit.

9. The sampling device of claim 1, further comprising:
a spring that biases at least the sample cuvette outwardly from the housing.

10. The sampling device of claim 1, wherein the respective ranges of wavelengths of at least two of the emitters at least partially overlap.

11. The sampling device of claim 1, further comprising:
the sample cuvette sized and dimensioned to be at least partially received by the sample chamber, at least a portion of the sample cuvette transmissive to at least some of the wavelengths of electromagnetic energy emitted by the emitters.

12. The sampling device of claim 1, wherein the optical portion of the electromagnetic spectrum extends from near-infrared through near-ultraviolet.

13. The sampling device of claim 1, further comprising:
at least one port providing flow-through, fluid communication with the cuvette.

14. The sampling device of claim 1, further comprising:
at least one control subsystem communicatively coupled to the emitters, the primary sampling sensors; and the calibration sensors; and
at least one temperature sensor communicatively coupled to the at least one control subsystem, wherein the at least one control subsystem controls operation based at least in part on information from both the calibration sensors and the at least one temperature sensor.

15. The sampling device of claim 14, wherein the at least one control subsystem calibrates an output value based at least in part on information from both the calibration sensors and the at least one temperature sensor.

16. The sampling device of claim 14, wherein the at least one control subsystem calibrates a drive signal supplied to at least one of the emitters based at least in part on information from both the calibration sensors and the at least one temperature sensor.

17. The sampling device of claim 14, wherein the sample chamber is rectangular, having two pairs of opposed walls.

18. The sampling device of claim 17, further comprising:
    the sample cuvette which is square and sized and dimensioned to be at least partially received by the sample chamber, at least a portion of the sample cuvette transmissive to at least some of the wavelengths of electromagnetic energy emitted by the emitters.

* * * * *